(12) United States Patent
Mendu et al.

(10) Patent No.: US 7,249,569 B2
(45) Date of Patent: Jul. 31, 2007

(54) METHODS FOR INJECTING AVIAN EGGS

(75) Inventors: Nandini Mendu, Chapel Hill, NC (US); Molly Bland, Cary, NC (US); Stephen Wolfe, Chapel Hill, NC (US); John Hebrank, Durham, NC (US); Dipak Mahato, Raleigh, NC (US)

(73) Assignee: Embrex, Inc., Research Triangle Park, NC (US)

( * ) Notice: Subject to any disclaimer, the term of this patent is extended or adjusted under 35 U.S.C. 154(b) by 505 days.

(21) Appl. No.: 10/216,427

(22) Filed: Aug. 9, 2002
(Under 37 CFR 1.47)

(65) Prior Publication Data

US 2003/0172392 A1  Sep. 11, 2003

Related U.S. Application Data

(60) Provisional application No. 60/312,015, filed on Aug. 13, 2001.

(51) Int. Cl.
*A01K 45/00* (2006.01)

(52) U.S. Cl. .......................... 119/6.8; 435/349; 800/21

(58) Field of Classification Search ................ 119/6.8; 800/21, 24, 25; 435/349
See application file for complete search history.

(56) References Cited

U.S. PATENT DOCUMENTS

| 3,120,834 A | 2/1964 | Goldhaft et al. |
| 3,256,856 A | 6/1966 | Nicely et al. |
| 3,256,876 A | 6/1966 | Elam |
| 4,917,045 A | 4/1990 | Wiegand et al. |
| 4,973,595 A | 11/1990 | Robel |
| 5,011,780 A | 4/1991 | Perry |
| 5,162,215 A | 11/1992 | Bosselman et al. |
| 5,339,766 A | 8/1994 | Phelps et al. |
| 5,340,749 A | 8/1994 | Fujiwara et al. |
| 5,438,954 A | 8/1995 | Phelps et al. |
| 5,444,045 A | 8/1995 | Francis et al. |
| 5,656,479 A | 8/1997 | Petitte et al. |
| 5,722,342 A | 3/1998 | Line et al. |

(Continued)

FOREIGN PATENT DOCUMENTS

CA    2300380 A1    2/2000

(Continued)

OTHER PUBLICATIONS

Bosselman et al., "Germline Transmission of Exogenous Genes in the Chicken," *Science* 243: 533-535 (1989).

(Continued)

*Primary Examiner*—Jeffrey L. Gellner
(74) *Attorney, Agent, or Firm*—Myers Bigel Sibley & Sajovec, P.A.

(57) ABSTRACT

The present invention provides improved methods of injecting an avian egg containing an embryo, preferably an early embryo (e.g., a blastoderm). The methods of the invention may be used to deliver a substance to an egg, remove a sample from an egg, and/or to insert a detector device into an egg to collect information therefrom. In preferred embodiments, the invention is used to deliver a substance to the embryo in ovo. In other preferred embodiments, the invention is used to produce chimeric or transgenic avian embryos in ovo.

60 Claims, 9 Drawing Sheets

U.S. PATENT DOCUMENTS

| | | | |
|---|---|---|---|
| 5,817,320 A * | 10/1998 | Stone | 424/278.1 |
| 5,830,510 A | 11/1998 | Petitte et al. | |
| 5,897,998 A | 4/1999 | Speksnijder et al. | |
| 5,945,577 A | 8/1999 | Stice et al. | |
| 5,994,619 A | 11/1999 | Stice et al. | |
| 6,032,612 A | 3/2000 | Williams | |
| 6,176,199 B1 | 1/2001 | Gore et al. | |
| 6,235,970 B1 | 5/2001 | Stice et al. | |
| 6,244,214 B1 | 6/2001 | Hebrank | |
| 6,286,455 B1 | 9/2001 | Williams | |
| 6,333,192 B1 | 12/2001 | Petitte et al. | |
| 6,397,777 B1 | 6/2002 | Andacht et al. | |
| 2001/0021528 A1 | 9/2001 | Petitte et al. | |
| 2002/0116732 A1 | 8/2002 | Christmann | |

FOREIGN PATENT DOCUMENTS

| | | |
|---|---|---|
| CA | 2307840 A1 | 4/2000 |
| EP | 0 746 976 A2 | 12/1996 |
| EP | 1 004 237 A2 | 5/2000 |
| WO | WO 90/03439 | 4/1990 |
| WO | WO 97/47739 | 12/1997 |
| WO | WO 98/27214 A1 | 6/1998 |
| WO | WO 98/30683 A3 | 7/1998 |
| WO | WO 98/37243 A1 | 8/1998 |
| WO | WO 99/01163 A1 | 1/1999 |
| WO | WO 99/06533 A1 | 2/1999 |
| WO | WO 99/06534 A1 | 2/1999 |
| WO | WO 00/75300 A3 | 12/2000 |
| WO | WO 01/62076 A1 | 8/2001 |

OTHER PUBLICATIONS

Thoraval et al., "Germline transmission of exogenous genes in chickens using helper-free ecotropic avian leucosis virus-based vectors," *Transgenic Research* 4: 369-376 (1995).

International Search Report, PCT/US02/24951, Dec. 18, 2002.

Petitte et al., "Production of somatic and germline chimeras in the chicken by transfer of early biastodermal cells," *Development* 108: 185-189 (1990).

Bednarczyk et al., *Improvement of Hatchability of Chicken Eggs Injected by Blastoderm Cells*, Poultry Science, 2000, vol. 79, pp. 1823-1828.

Jia et al., "Studies on Cultivation of Chick Embryos and Production of Chimeric Chickens", *China Journal of Lab Animal Science*, 2001, vol. 11(2), p. 93-94.

* cited by examiner

Egg Preparation

Introducing Opening Into Egg

Locating Embryo

Inserting Device

METHODS FOR INJECTING AVIAN EGGS

RELATED APPLICATION INFORMATION

This application claims the benefit of U.S. Provisional Application No. 60/312,015 filed Aug. 13, 2001, which is incorporated by reference herein in its entirety.

STATEMENT OR FEDERAL SUPPORT

The present invention was made, in part, with the support of grant number 70NANB1H3017 from the Advanced Technology Program, National Institute of Science and Technology. The United States government has certain rights to this invention.

FIELD OF THE INVENTION

The present invention relates to methods of manipulating an egg containing an embryo and, in particular, to methods of introducing material into or removing material from an egg containing an avian embryo.

BACKGROUND OF THE INVENTION

There are a number of applications for which it is desirable to inject eggs containing early avian embryos. For example, it may be desirable to deliver a substance to an early embryo, such as a blastoderm. To illustrate, it may be desirable in the poultry industry to manipulate an early embryo in ovo to introduce a foreign nucleic acid molecule (i.e., to create a transgenic bird) or to introduce a foreign cell(s) (i.e., to create a chimeric bird) into the developing embryo.

Likewise, improved methods of injecting eggs containing an early embryo may be used to remove samples from eggs, including samples of embryonic and extra-embryonic materials. Further, for other applications it may be desirable to insert a sensing device inside an egg containing an embryo to collect information therefrom.

Current methods of manipulating bird eggs containing early embryos may be undesirable because they may result in unacceptably low hatch rates. It has been suggested that depressed hatch rates are a result of the opening made in the egg shell, introduction of air bubbles into the egg, damage to the extra-embryonic membranes or to the embryo itself, or a combination of these factors.

Accordingly, there is a need in the art for improved methods of manipulating avian eggs containing early embryos.

SUMMARY OF THE INVENTION

The present invention provides a method of manipulating avian eggs containing embryos, in particular early stage embryos, which may result in reduced trauma to the embryo and improved viability and hatch rates. Accordingly, the present invention provides improved methods of inserting or implanting a variety of devices (e.g., a delivery device, sampling device, and/or a detector device, and the like) into an avian egg containing an embryo, in particular an early embryo (e.g., a blastoderm), which may result in lower levels of morbidity and mortality among the manipulated embryos. The methods of the invention are particularly useful in methods of delivering vaccines, vitamins, growth promoting hormones and growth factors, enzymes, cytokines, nucleic acids, and/or cells to a bird in ovo. For example, the method may be used to produce a chimeric bird (i.e., containing foreign cells) or a transgenic bird (i.e., containing a foreign nucleic acid sequence). The methods of the invention are also useful for collecting samples or information from a bird in ovo, for example, for use in methods of gender sorting, determining embryo viability, and/or obtaining information about the genetic profile of the embryo.

The methods of the invention may be carried out on a single egg or a plurality of eggs. Moreover, the inventive methods may be manual, automated, or semi-automated.

Accordingly, as a first aspect, the present invention provides a method of injecting an avian egg, comprising the steps of: orienting an avian egg containing a blastoderm in a predetermined position; introducing a small opening into a shell of the egg; extending a device through the opening in the egg shell; piercing an inner shell membrane with the device, wherein the inner shell membrane is essentially intact prior to inserting the device therethrough; and retracting the device from the egg.

The device may be, for example, a delivery device, a sampling device, or a detector device. Preferably, the opening in the egg shell is made at the blunt end of the egg over the air cell.

As a further aspect, the present invention provides a method of injecting an avian egg, comprising the steps of: orienting a blunt end of an avian egg in a predetermined position, the avian egg containing (i) a blastoderm and (ii) an air cell; introducing a small opening into a shell of the egg at the blunt end of the egg over the air cell; introducing a small opening in an outer shell membrane under the small opening in the egg shell; extending a delivery device through the openings in the egg shell and the outer shell membrane; piercing an inner shell membrane with the delivery device, wherein the inner shell membrane is essentially intact prior to inserting the delivery device therethrough; releasing a substance through the delivery device and depositing the substance in a location in the blastoderm or in close proximity thereto; and retracting the delivery device from the egg. In particular embodiments, the egg is oriented in a generally upward position.

As a still further aspect, the present invention provides a method of injecting an avian egg, comprising the steps of: orienting an avian egg containing a blastoderm in a predetermined position; introducing a small opening into a shell of the egg; extending a sampling device through the opening in the egg shell; piercing an inner shell membrane with the sampling device, wherein the inner shell membrane is essentially intact prior to inserting the sampling device therethrough; removing a sample from the egg with the sampling device; and retracting the sampling device from the egg.

As yet a further aspect, the present invention provides a method of injecting an avian egg, comprising the steps of: orienting an avian egg containing a blastoderm in a predetermined position; introducing a small opening into a shell of the egg; extending a detector device through the opening in the egg shell; piercing an inner shell membrane with the detector device, wherein the inner shell membrane is essentially intact prior to inserting the detector device therethrough; detecting with the detector device information from the interior of the egg; and retracting the detector device from the egg.

As described in more detail below, the present invention may be advantageously employed for any application in which it is desirable to manipulate the contents of an avian egg containing an early embryo (e.g., a blastoderm) or to obtain information therefrom. In particular, the invention may be used to produce transgenic or chimeric embryos or to carry out any chromosomal or DNA based determinations (e.g., gender sorting or to evaluate the genetic profile of the embryo). Alternatively, the invention may be practiced to remove a sample of any embryonic or extra-embryonic fluid or tissue from an avian egg containing an early embryo. Additionally, or alternatively, the invention may be carried out to obtain information from the egg or the embryo, which method may be used in conjunction with delivery or sampling methods.

These and other aspects of the present invention are set forth in more detail in the description of the invention that follows.

DETAILED DESCRIPTION OF THE INVENTION

Figure 1:
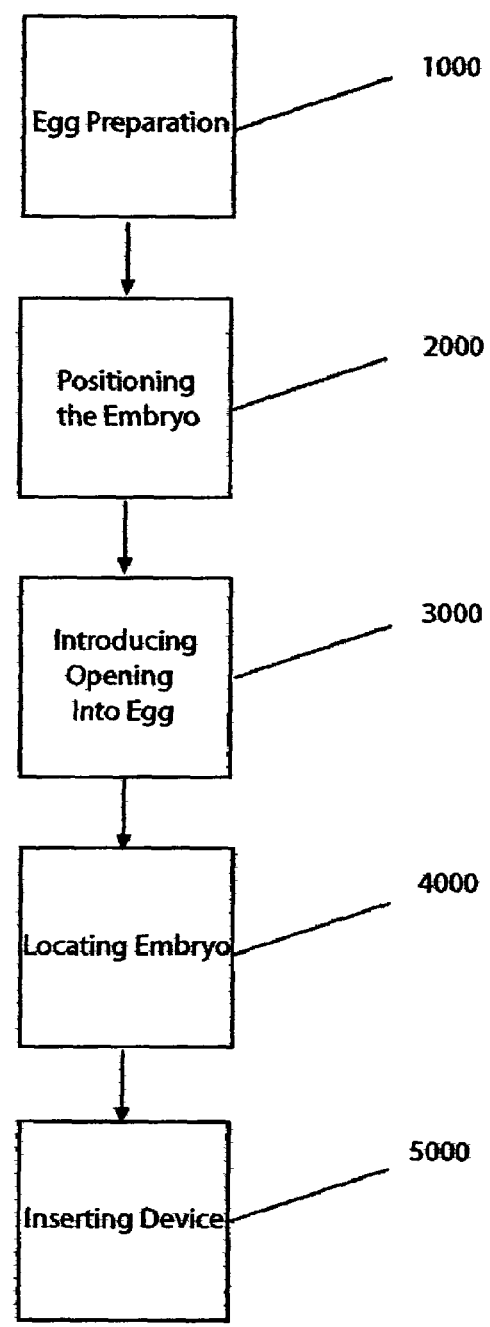
FIG. 1 is a flow chart that illustrates methods of manipulating eggs according to the present invention.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

It should be noted that, in some alternative embodiments of the present invention, the functions noted in the blocks of the flow charts of FIGS. 1-6 may occur out of the order noted. For example, two or more blocks shown in succession may in fact be executed substantially concurrently or the two or more blocks may sometimes be executed in the reverse (or otherwise different) order. Furthermore, in certain embodiments of the present invention, functions illustrated in FIGS. 1-6 may be performed in parallel or sequentially. Moreover, in other embodiments, certain blocks may be omitted altogether.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a", "an" and "the" are intended to include the-plural forms as well, unless the context clearly indicates otherwise.

All publications, patent applications, patents, and other references mentioned herein are incorporated by reference in their entirety.

The term "avian" and "avian subjects," as used herein, is intended to include males and females of any avian species, but is primarily intended to encompass poultry which are commercially raised for eggs, meat or as pets. Accordingly, the terms "avian" and "avian subject" are particularly intended to encompass chickens, turkeys, ducks, geese, quail, pheasant, parakeets, parrots, cockatoo, cockatiel, ostrich, emu and the like. Chickens and turkeys are the preferred avian subjects, with chickens being most preferred. Alternatively, the avian or avian subject is an endangered species of bird.

The present invention provides improved methods of manipulating an egg containing an avian embryo. By "manipulating" or "manipulation" it is meant that openings are made in the egg shell, the outer shell membrane, and the inner shell membrane of the egg and a substance or device is implanted or inserted therein.

As used herein, the term "early embryo" refers to an avian embryo from the time of lay (blastodermal stage) through about the developmental stage where primordial germ cells (PGCs) are migrating. With particular respect to chicken embryos, an "early embryo" is generally about an embryonic stage 20 (H&H) embryo or earlier. The developmental stages of the chicken embryo are well-understood in the art, see e.g., The Atlas of Chick Development, R. Bellairs & M. Osmond, eds., Academic Press, 1998. In particular embodiments, the early chicken embryo is about a stage 4 to about a stage 18 embryo, or about a stage 12 to about a stage 17 (H&H) embryo or, alternatively, about a stage 13 to about a stage 15 (H&H) embryo (for example, for the delivery of PGCs). In other particular embodiments, the early embryo is a blastoderm stage embryo, as described below.

As used herein, the term "blastoderm" has its understood meaning in the art. Generally, in the practice of the instant invention, a blastoderm includes an embryo from the time of lay through the end of gastrulation. The blastoderm is sometimes referred to by the alternative designations "germinal disc" or "embryonic disc" in the art. A blastoderm may be described as a flattened disc of cells that forms during cleavage in the early embryo and persists until the end of gastrulation. By the time of laying two major regions of the blastoderm are visible, the centrally-situation area pellucida and the peripherally-located area opaca (The Atlas of Chick Development, R. Bellairs & M. Osmond, eds., Academic Press, 1998). With particular respect to chicken embryos, the blastoderm is typically characterized as an embryo from the time of lay (i.e., Stage IX or Stage X EG&K) through about stage XII (EG&K). In particular embodiments of the invention, the chicken embryo is about a stage VIII through about a stage XIII (EG&K) embryo, or alternatively, about a stage IX through about a stage XII (EG&K) embryo. In other embodiments, the chicken embryo is about a stage X to about a stage XI (EG&K) embryo. In still other embodiments, the chicken embryo is about a stage X (EG&K) embryo.

Currently used methods of manipulating eggs containing early embryos may not be satisfactory for commercial purposes in that they may result in unacceptably high levels of morbidity and mortality. In particular embodiments, the avian embryo may be transgenic (i.e., contain a foreign nucleotide sequence).

By injection or insertion of the device in "close proximity to" the embryo or blastoderm it is meant that the device is injected or inserted right above, below or adjacent to the early embryo or blastoderm or in the surrounding structures, e.g., within about 10, 8, 5, 3, 2 or 1 mm or less of the early embryo or blastoderm. The term in "close proximity" to the blastoderm," encompasses injection or insertion of a device into the subgerminal cavity of the embryo, between the area opaca and the vitelline membrane, between the area pellucida and the vitelline membrane, and/or between the area opaca and the area pellucida.

As used herein, the terms "injection" and "injecting" encompass methods of inserting a device (typically an elongate device) into an egg or embryo, including methods of delivering or discharging a substance into an egg or embryo, methods of removing a substance (i.e., a sample) from an egg or embryo, and/or methods of inserting a detector device into an egg or embryo.

The terms "chimeric bird" or "chimeric embryo" refer to a "recipient bird" or embryo, respectively, that contains cells (i.e., somatic cells and/or gametes) from another bird or embryo, referred to as a "donor." The resulting chimeric bird or embryo will typically contain cells derived from both the recipient and the donor. In particular embodiments, at least about 5%, 10%, 25%, 35%, 50%, 65%, 75%, 85%, 90%, 95% or more of the somatic cells in the chimeric bird may be derived from the donor. Likewise, in other embodiments, essentially all of the somatic cells are derived from the donor. In yet other particular embodiments, at least a portion of the gametes (e.g., at least about 5%, 10%, 25%, 35%, 50%, 65%, 75%, 85%, 90%, 95% or more) in the chimeric bird or embryo are derived from the donor. In other particular embodiments, essentially all of the gametes are derived from the donor.

The terms "transgenic bird" and "transgenic embryo" are used herein in accordance with their generally understood meanings in the art. A transgenic bird or transgenic embryo contains a foreign nucleic acid sequence in one or more cells. The foreign nucleic acid may from a different species (e.g., avian, mammalian, insect, bacterial, protozoan, yeast, fungal, viral) or from the same species. For example, an additional copy of a wild-type coding sequence or a mutated form of a coding sequence from the same species may be introduced. The foreign nucleic acid may encode a polypeptide, an antisense RNA or other untranslated RNA, as described in more detail below. The foreign nucleic acid is generally stably transformed into one or more cells in the transgenic bird or embryo, e.g., by stable integration into the genome or by introduction of an episomal construct that is stably maintained by the host cell.

As used herein, the term "predetermined location" indicates a fixed position or depth within an egg. For example, a device may be inserted into an egg to a fixed depth and/or fixed position in the egg (e.g., the egg may be placed in a predetermined orientation and the device is inserted into the egg at a fixed point to a fixed depth). In alternative embodiments, the injection may be carried out based on information obtained from the egg, for example, regarding the position of the embryo (e.g., blastoderm) or a compartment therein, the vitelline membrane and the like within the egg (for example, the position of a desired compartment may be determined using a sensor or probe and the device is inserted based on that information).

The term "essentially intact" when used to describe the egg shell or the inner or outer shell membrane indicates that there are no significant perforations or tears therethrough. The term "essentially intact" when used to describe the inner shell membrane indicates that there are no significant perforations or tears in the inner shell membrane. Typically, the only portion of the inner shell membrane that will be visible is beneath the window or opening formed in the egg shell, and the condition of the inner shell membrane is determined with respect to this exposed portion beneath the opening.

U.S. Pat. No. 5,897,998 (Speksnijder) describes a method for manipulating the contents of an avian egg by making an opening in the shell of an egg positioned in a horizontal position with respect to its long axis, and wherein the opening is made in the egg shell on the top side of the egg. A drop of liquid is then placed over the opening in the egg shell "such that the opening is completely covered" (U.S. Pat. No. 5,897,998; Abstract). The underlying membranes are then cut away, and a solution may be microinjected through the openings in the shell and membranes into the egg, and the opening sealed.

The present inventors have found that it is not necessary to insert a device into the egg through a drop of liquid. Moreover, if liquid is deposited, it need not cover the entire surface of the exposed membranes and the opening in the egg shell as taught by U.S. Pat. No. 5,897,998. Further, the inventors have found that survival of the manipulated embryos may be improved by leaving at least the inner egg shell membrane essentially intact prior to insertion of the device into the egg.

To illustrate, in a preferred and exemplary method of introducing a substance into an avian egg, the egg is oriented in a predetermined position, a small opening is made into the shell of the egg such that the inner shell membrane is maintained essentially intact prior to injection. A delivery device is extended through the opening in the egg shell, and the inner shell membrane is pierced with the delivery device (e.g., a micropipette or microinjection needle) and a substance is released through the delivery device and deposited into a desired location within the egg. The substance will generally be released in a predetermined dosage in a volume of from approximately one to twenty microliters (typically, less than 5 or 10 microliters). The volume to be delivered is not critical as long as it does not unduly harm the embryo and is effective for delivery.

By a "small opening" in the egg shell, it is meant an opening that is sufficiently small that it does not unduly harm the developing embryo and can be sealed or otherwise closed if so desired. In particular embodiments, the "small opening" in the egg shell may be about 35 mm or less in diameter, for example, from about 10 mm to about 30 mm in diameter or about 15 mm to about 25 mm in diameter. In still other embodiments, the "small opening" is less than about 10 mm, less than about 5 mm, or less than about 3 mm, 2 mm or even 1 mm in diameter.

Typically, the delivery device will be retracted from the egg, unless the delivery device is an implantable device that is left within the egg. Generally, the opening in the egg shell is sealed, unless a self-sealing material (i.e., a sealant) has been applied to the egg shell prior to introducing the opening therein. The manipulated egg may then be placed in an incubator or otherwise stored until hatch or whatever other desired endpoint.

The opening in the egg shell may be made in any suitable location, e.g., in the side of the egg near the equatorial axis or at either end of the egg. In a particular preferred embodiment of the invention, the opening in the egg shell is introduced at the blunt end of the egg over the air cell. According to this embodiment, a small opening is also introduced into the outer shell membrane. The inner shell membrane, which is separated from the outer shell membrane by the air cell, is left essentially intact prior to injection. The inner shell membrane is pierced by the delivery device and a substance is released therethrough into a desired location in the egg.

A "small opening" in the outer shell membrane is essentially as described above for a small opening in the egg shell.

Those skilled in the art will appreciate that the early embryo (e.g., blastoderm) will typically locate itself in an area at or near the uppermost portion of the egg, whether the egg is positioned horizontally, vertically, or at an angle. Thus, the opening in the egg shell will generally be made in the uppermost portion of the egg near whether the early embryo (e.g., blastoderm) is expected to locate unless measures are taken to steer the embryo to a different position within the egg.

In particular embodiments, the opening in the egg shell is made in the upper side of the egg (i.e., along the long axis of the egg). According to this embodiment, the egg will typically be oriented in a generally horizontal position, i.e., with the long axis tilted at an angle of less than about 45 degrees from horizontal. In particular embodiments, the egg is tilted less than about 30, 20, 15, 10 or 5 degrees from horizontal with respect to the long axis of the egg. In other embodiments, the egg is placed in a substantially horizontal position, i.e., essentially without tilting the egg along its long axis (e.g., tilted less than about 5% or 10% from horizontal).

When injecting into the side of the egg, the device will generally be inserted concurrently through both the inner and outer shell membranes. In other particular embodiments, the membranes may be removed when the opening is made in the egg shell. In still other embodiments, an opening is made in the outer shell membrane prior to inserting the device through the inner shell membrane, where the inner shell membrane is essentially intact prior to inserting the device therethrough.

In particular preferred embodiments, the egg is oriented in a vertical position with respect to the long axis of the egg, with the blunt end of the egg oriented in a generally upward position. By a "generally upward position" it is meant that the egg is positioned vertically, and the long axis is tilted at an angle of less than about 45 degrees from vertical. In particular embodiments, the egg is tilted less than about 30, 20, 15, 10 or 5 degrees from vertical with respect to the long axis of the egg. In other embodiments, the egg is placed in a substantially upright position, i.e., essentially without tilting the egg along its long axis (e.g., tilted less than about 5% or 10% from vertical). According to this embodiment, the egg is generally tilted an egg such that the early embryo (e.g., blastoderm) is located beneath the air cell at the blunt end of the egg.

The opening in the egg shell membrane may be made in a predetermined position (e.g., in the center of the blunt end of the egg or in the center of the air cell at the blunt end of the egg) or may be made in a position that is determined, at least in part, by the position of the early embryo (e.g., blastoderm) within the egg.

The present invention may be advantageously used to deliver or remove substances to or from an early embryo (as described above) in ovo. In particular embodiments, the early embryo is a blastoderm (also as described above). It is also preferred that the early embryo is at a stage at which the air cell is detectable within the egg.

The substance may be released into the embryo (e.g., blastoderm) itself (e.g., into the area pellucida or the area opaca). Alternatively, the substance may be released in close proximity to (e.g., right above, below or adjacent to) the early embryo, e.g., within about 10, 8, 5, 3, 2 or 1 mm or less from the embryo (e.g., blastoderm). According to this embodiment, the substance may be released into the sub-germinal cavity of the embryo, between the area opaca and the vitelline membrane, between the area pellucida and the vitelline membrane, and/or between the area opaca and the area pellucida. In still other embodiments of the invention, the substance is released into the latebra, and/or into the nucleus of pander.

Methods of delivering PGCs are known in the art and are generally carried out by injecting the PGCs into a blood vessel in the embryo (e.g., the dorsal aorta) or any sufficiently large vessel in the extra-embryonic membranes (see, e.g., patent publication WO 99/06533; University of Massachusetts). Likewise, a blood sample can be removed from the blood vessel in the embryo or a vessel in the extra-embryonic membranes of a PGC stage embryo.

In one particular embodiment, the present invention provides a method of delivering a substance to an avian egg comprising an early embryo (e.g., a blastoderm) and an air cell, the method comprising: orienting the egg so that the blunt end of the egg is in a predetermined position (e.g., in a generally upward position, as defined above), introducing a small opening in the egg shell and the outer shell membrane at the blunt end of the egg over the air cell, where the inner shell membrane is maintained in an essentially intact condition, extending a delivery device through the openings in the shell and the outer shell membrane, piercing the inner shell membrane with the delivery device, and releasing a substance through the delivery device and into the blastoderm or in close proximity thereto.

The step of forming the opening in the outer shell membrane and piercing the inner shell membrane may be performed essentially concurrently by inserting the device through the two membranes. In particular embodiments, an opening will first be made in the outer shell membrane, and then the device will be inserted through the inner shell membrane to create an opening therein. Likewise, the opening in the egg shell may be formed p prior to (e.g., first an opening is punched into the egg shell and then an opening is put in the outer shell membrane) or essentially concurrently with the formation of the opening in the outer shell membrane (i.e., as a single step).

As described above, it is preferred that the injection through the inner shell membrane is not made through a droplet of liquid that has been deposited on the inner shell membrane. In those embodiments in which injection is made through a liquid, it is preferred that the liquid is an aqueous liquid (e.g., an albumen solution) and that only a small volume (e.g., two to ten microliters) is deposited onto the inner shell membrane.

Those skilled in the art will appreciate that the methods of the present invention may be carried out on a plurality of bird eggs, e.g., in a commercial poultry operation. When the inventive methods are carried out on a plurality of bird eggs, an improved hatch rate and reduced morbidity may be observed in the flock as a whole, although there may still be morbidity and mortality in individual birds that were subjected to manipulation in ovo.

Preferably, the hatch rate in the manipulated eggs is at least about 40%, 50%, 60%, 65%, 70%, 75%, 80%, 85%, 90%, 95% or higher. It is also preferred that the hatch rate in the manipulated eggs is similar to that observed in control eggs that were not subjected to manipulation (e.g., no openings made in the shell, etc.), or the hatch rate is depressed by less than about 25%, 15%, 10%, 5%, 3%, 2% or even 1% as compared with the control eggs.

In particular embodiments, the invention may be used to deliver a substance to an egg containing an early embryo (e.g., a blastoderm) or to deliver a substance to the early embryo itself. Any substance may be injected by embodiments of the present invention, including but not limited to cells, vaccines, polypeptides, growth-promoting agents, probiotic cultures such as competitive exclusion media, antibiotics, heterologous nucleotide sequences including gene transfer vectors, vitamins, and/or markers such as dyes, etc. The substances may be injected alone, or in combination (e.g., antibiotics may be included with the delivery of other substances). As another illustrative example, a dye or other marker may be included with other substances to be delivered to provide a means of determining whether delivery was to the desired location.

As used herein, a "polypeptide" encompasses both proteins and peptides. Polypeptides to be delivered to the egg or to the embryo itself include antibodies, antigens (e.g., for immunization), growth factors, hormones, and other growth or performance enhancing polypeptides, enzymes, cytokines, and the like.

By "growth or performance enhancing" it is meant that the rate of growth, the final size of the animal, feed to gain ratio, egg production, meat production, and the like, is improved.

Vaccine organisms include dead, live or attenuated viruses, bacteria, protozoa, and fungi, including the various life stages of these different organisms.

The method may also be advantageously used to introduce a nucleotide sequence of interest into the developing embryo (preferably, the nucleotide sequence is stably transformed into the embryonic cells), i.e., to create a transgenic bird (as defined above). Those skilled in the art will appreciate that it is not necessary that every cell of the resulting transgenic bird contain the transgene. The nucleotide sequence may be DNA or RNA, and it may encode any polypeptide of interest or may encode a non-translated RNA (e.g., antisense RNAs or ribozymes). In those embodiments wherein the nucleotide sequence encodes a polypeptide, the polypeptide may be a reporter polypeptide (e.g., an enzyme such as Green Fluorescent Protein or alkaline phosphatase), a therapeutic polypeptide, an immunogenic polypeptide (i.e., for vaccination), a growth or performance enhancing polypeptide, and the like.

The nucleotide sequence may be introduced into the embryo using any vector and method known in the art. For example, a viral vector (e.g., retrovirus) or DNA vector may be used to carry the foreign nucleotide sequence of interest. In particular embodiments, a viral vector is not used to introduce the nucleotide sequence into the embryo. Methods of viral transduction and introduction of naked DNA vectors into cells (e.g., using liposomes or electroporation) are known in the art. Suitable apparatus for in ovo electroporation include the BTX ECM 2001 electroporation device (www.genetronics.com).

In other preferred embodiments, the present invention is used to introduce a foreign or "donor" cell into a recipient embryo (i.e., to create a chimeric embryo and, optionally, a chimeric bird, as defined above). The donor cell may be a transgenic cell or have any other characteristic of interest for introduction into an embryo. The donor cell will typically be an avian cell, as described above.

In particular embodiments, the recipient embryo and the donor cell are from the same avian species. Alternatively, the donor cell may be from a different avian species from the recipient embryo (e.g., putting a turkey cell into a chicken embryo). As a further alternative, the embryo and donor cells may be from the same avian species, but be from different strains or breeds (e.g., two different breeds or strains of chicken). The recipient or donor cell may be from an endangered species of bird.

Furthermore, the donor cells may also be from a high performing or elite pedigree bird. Typically, high performing or elite pedigree birds are used as breeding stock to create lines with desired traits. The present invention advantageously allows for direct transfer of cells (and therefore, genetic material) from a single high performing or elite pedigree bird to produce numerous "progeny" in a single step rather than by the conventional process of expanding the line through successive generations, which may result in dilution or loss of some of the desired traits. The high performing or elite pedigree birds may be improved or superior for any desired trait (e.g., a commercially important trait), including but not limited to increased muscle production, reduced fat composition, increased egg production, improved disease resistance, altered size (e.g., smaller birds), reduced feather reduction or altered feather composition, and/or altered proportion of male birds.

Typically, the donor cell will be selected from the group consisting of a blastodermal cell, a stem cell, a cultured stem cell, an embryonic stem cell, a primordial germ cell, and an embryonic germ cell.

In some embodiments, it may be desirable to compromise the cells in the recipient embryo prior to introduction of the donor cells. Methods of compromising embryonic cells are known to those skilled in the art. Suitable methods of compromising the embryo include but are not limited to coring (removing cells from recipient embryo), mechanical injury (e.g., tearing), gamma-irradiation, microwaves, soft x-rays, chemical treatment (e.g., ammonia gas), heat, laser treatment, and/or cryogenic cooling, and the like. In particular embodiments, irradiation, heating, chemical treatment, and soft x-rays may be applied to the whole egg. Ultraviolet radiation, microwaves, heat, laser treatment, cryogenic treatment, mechanical injury, and coring may be used in other embodiments through a window in the egg shell to compromise the embryo.

The extent to which the embryo is compromised may be determined by any method known in the art, e.g., by using dyes, in particular fluorescent dyes, that selectively stain necrotic (e.g., propidium iodide) or apoptotic cells (e.g., Hoeschst 333342 stain). Alternatively, mRNA transcripts or polypeptides may be detected which are indicative of a necrotic or apoptotic state as known in the art.

Accordingly, in a preferred embodiment, the present invention provides a method of producing a chimeric bird, comprising the steps of introducing a small opening into the shell of the egg, extending a delivery device through the opening in the egg shell, piercing the inner shell membrane with the delivery device, wherein the inner shell membrane is essentially intact prior to inserting the delivery device therethrough, releasing an avian donor cell through the delivery device and depositing the donor cell into the blastoderm or in close proximity thereto (as described above) under conditions sufficient to result in a chimeric embryo, retracting the delivery device from the egg and incubating the chimeric embryo to hatch to result in a chimeric bird.

Successful delivery of the cells to the blastoderm and/or chimera production may be assessed by any method known in the art. For example, the donor cells may be contacted with a dye (e.g., fluorescent dye such as carboxyfluorescein-diacetate-succinyl-ester), gold particles, or any other marker known in the art that may be detected after delivery of the cells to the recipient embryo. Alternatively, the donor cells may carry particular epitopes or nucleic acid sequences that may be detected using antibodies or standard nucleic acid detection methods to identify the presence of the donor cell or progeny thereof in the blastoderm, the embryo or the resulting bird. Additionally, or alternatively, the donor cells may carry a gene(s) conferring a particular phenotypic trait that may be readily detected in the embryo or the bird after hatch (e.g., feather color).

The foregoing description of the invention has primarily been with respect to methods of delivering a substance to an egg or to an early embryo (e.g., blastoderm). The methods of injecting an egg may also be carried out to insert a sampling device into the egg to remove a substance (i.e., a sample) from the egg (e.g., from the embryo, as described above) and/or to detect information from the egg (e.g., from the embryo).

In one embodiment, a sampling device may be inserted into the egg to remove a sample therefrom. The sample may be taken from the extra-embryonic portions of the egg (e.g., the yolk or the albumen). For example, a sample may be taken from the albumen to determine the presence or absence of microbial contamination (e.g., *Salmonella*) therein. In other embodiments, the sample is taken from the early embryo (e.g., blastoderm), such as from the area pellucida, the area opaca, and/or the subgerminal cavity. In embodiments of the invention, the sample contains blastodermal cells. Typically, the sample will be removed to obtain information therefrom. The sample may be removed, for example, in connection with methods of sexing or determining the viability of the embryo. To illustrate, a sample containing cells may be removed from the embryo, and the cells may be analyzed (typically after removal from the egg) to detect the sex chromosomes or sex-specific sequences on the chromosomes, as known by those skilled in the art. The sample may also be used for any other DNA based assay, e.g., to determine the presence of a particular gene or allele of interest in the embryo.

In another embodiment, a detector device may be inserted into the egg to detect information therein (i.e., from the egg and/or from the embryo). The detector may be inserted into an extra-embryonic location of the egg (e.g., the yolk or the air cell). Alternatively, the detector may be placed in close proximity (as defined above) to the embryo. In other embodiments, the detector may be placed into the area pellucida or the area opaca of the embryo or into the subgerminal cavity.

The detector device may be used to collect information including, but not limited to, the size of the embryo, the location of the embryo, the developmental stage of the embryo, the sex of the embryo, and/or the viability of the embryo. Preferably, the detector device obtains information regarding the location of the embryo and the subgerminal cavity. The information may be captured by an instrument (e.g., a computer or other data processor) that is connected to the detector.

For particular embodiments, the egg is identified from which a sample will be removed or information will be detected with a detector. Information regarding the sample or information obtained by the detector may be stored in association with the identification of the egg. Exemplary detector devices are discussed in more detail below.

FIGS. 1-6 are flow charts that illustrate particular embodiments of the invention.

As shown in FIG. 1, one particular method of injecting an avian egg containing an early embryo (e.g., a blastoderm) according to the invention comprises the steps of preparing the egg prior to injection 1000, positioning the embryo within the egg 2000, introducing an opening into the egg 3000, locating the embryo position 4000, and inserting a device into a desired location within the egg 5000.

Figure 2:
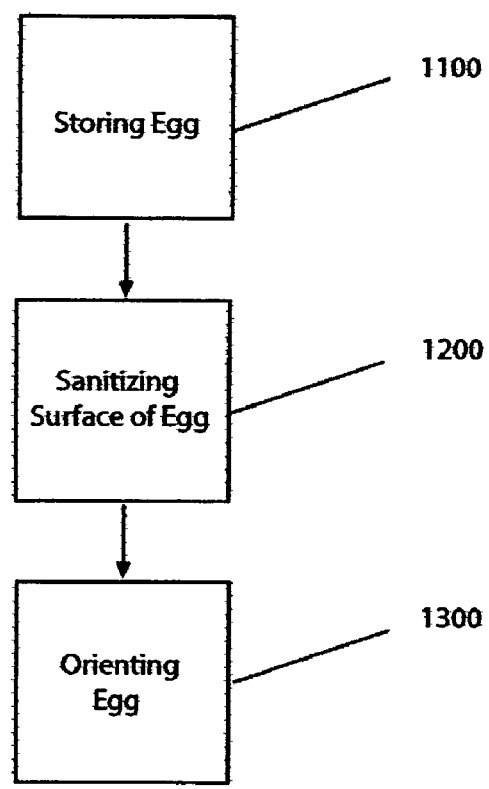
FIG. 2 is a flow chart that illustrates methods of preparing an egg prior to injection according to embodiments of the present invention.

As shown in FIG. 2, the egg is optionally prepared prior to injection. The surface of the egg, at least around the site of injection, is sanitized to reduce microbial contamination 1200 (e.g., with an alcohol or other sanitizing solution). The egg may further be oriented in a predetermined position 1300 (e.g., with the blunt end of the egg in a generally upward position). In particular embodiments, the egg is stored 1100 prior to injection. Typically, the egg is stored for a period of time that is sufficient to assist in positioning or "steering" the embryo to a desired position within the egg, but insufficient to result in an unacceptable incidence of morbidity or mortality to the embryo. To illustrate, the egg may be stored from about six, twelve, twenty-four hours or longer. There is no particular limit to the storage period as long as viability is not unduly impaired or the embryo does not develop beyond a suitable point for the present methods. Eggs may be stored for as long as about thirty or even about sixty days prior to injection. In embodiments of the invention, the egg is stored for about thirty days or less, about 14 days or less, about 10 days or less, or about 7 days or less prior to injection. In other particular embodiments, the egg is stored for about 1, 2, 3, 4, 5, 7, 8, 10, 14 or 21 days prior to injection; alternatively, about 1-21 days, about 1-14 days, about 1-7 days, about 1-4 days, about 4-8 days, or about 6-12 days prior to injection.

Generally, the egg is stored at conditions (e.g., temperature) that will not promote the development of the embryo within the egg or will avoid development beyond the desired developmental stage (e.g., the blastodermal stage). Those skilled in the art will appreciate that some cell division may occur during the storage period; however, in general, the development of the embryo is suspended or significantly delayed during the storage period.

The egg may be oriented in a horizontal or vertical position (with respect to the long axis) or at an angle therefrom during the storage period. In particular embodiments, the egg is stored in the same orientation as used for injection. Further, the egg may be held in a fixed position (e.g., within a device) in which both side-to-side movement and rotation around the long axis of the egg are restricted or prevented.

In particular embodiments, the embryo may further be compromised prior to injection into the embryo, as described above.

Figure 3:
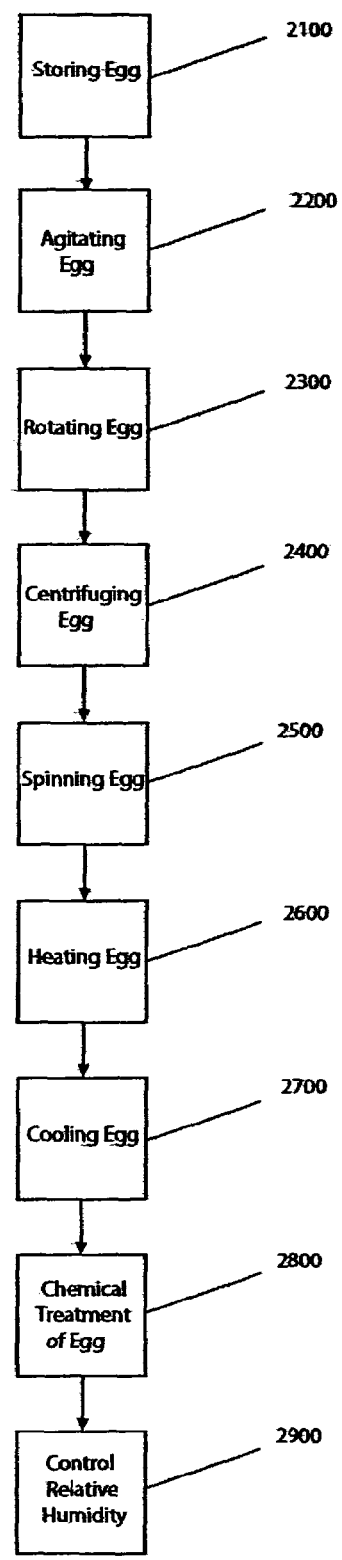
FIG. 3 is a flow chart that illustrates methods of steering or positioning an embryo in a desired location prior to injection according to embodiments of the present invention.

As indicated in the previous paragraph, it is often desirable and advantageous to steer or position the embryo prior to injection, in particular, for automated or semi-automated methods of injecting the egg. Turning to FIG. 3, as described above, the egg may be stored prior to injection 2100 to promote positioning of the blastoderm on the top center surface of the yolk. Alternatively, or concurrently, the egg may be agitated (e.g., shaken) 2200, rotated 2300, centrifuged 2400 and/or spun 2500 to assist in steering the embryo. Alternatively or additionally, the contents of the egg may be subjected to altered temperature conditions by heating 2600 (e.g., to a temperature from about 55° F. or 60° F. and below about 75° F., 80° F. or 95° F.) or cooling 2700. A discussed above, in heating the egg, it will be appreciated by those skilled in the art that the egg is subjected to a sufficiently mild heat treatment (time x temperature) such that the embryo does not develop beyond the desired stage. As still further alternative or additional treatments, the egg may be chemically treated (e.g., chemically treating the albumen with ammonia gas) 2800 to facilitate steering the embryo to a desired location. Additionally, or alternatively, the relative humidity of the air surrounding the egg may be controlled 2900 (e.g., to above or below about 75%).

In particular embodiments, eggs are subjected to treatments (e.g., chemical or mechanical) that result in a thinning of the albumen (i.e., loss of firmness or reduced Haugh Units in a broken egg). It is believed that blastoderm positioning at the top center surface of the yolk may be facilitated by a thinner albumen. Alternatively, eggs from older flocks and/or larger eggs may be used in the methods of the present invention. Eggs produced by older layers and larger eggs are both more likely to have a relatively thin albumen.

Ammonia gas has been reported in the literature to result in a thinning of the albumen. The egg may be exposed to any suitable level of ammonia gas that results in positioning of the blastoderm in a desired location. Suitable concentrations of ammonia gas may be less than about 100, 150, 250, 500, 750, 1000, 1500, 2000, 2500, 3000 or 3500, 4000, 5000, 6000, 7000, or 8000 mg/kg or higher for a sufficient period of time (e.g., about 0.25, 0.5, 1, 1.5, 2, 3, 4, 5 or 6 hours). In particular embodiments, the eggs are exposed to relatively high levels of ammonia gas (e.g., about 2000 to 4000 mg/kg) for a relatively short period of time (e.g., about 0.5 to about 1 hour). In other embodiments, the eggs are exposed to lower dosages of ammonia gas of about 250-1000 or about 500-1500 mg/kg for periods of about 0.5 to 2 hours.

In particular embodiments, a combination of approaches is taken to help position or steer the blastoderm to the top center surface of the yolk. For example, in one particular embodiment, the eggs are stored from about 2 to about 7 days at about 65° C. to about 75° C. while concurrently turning eggs during the storage period. Further, the eggs that are selected for this treatment may be larger eggs and/or eggs from older layers.

Figure 4:
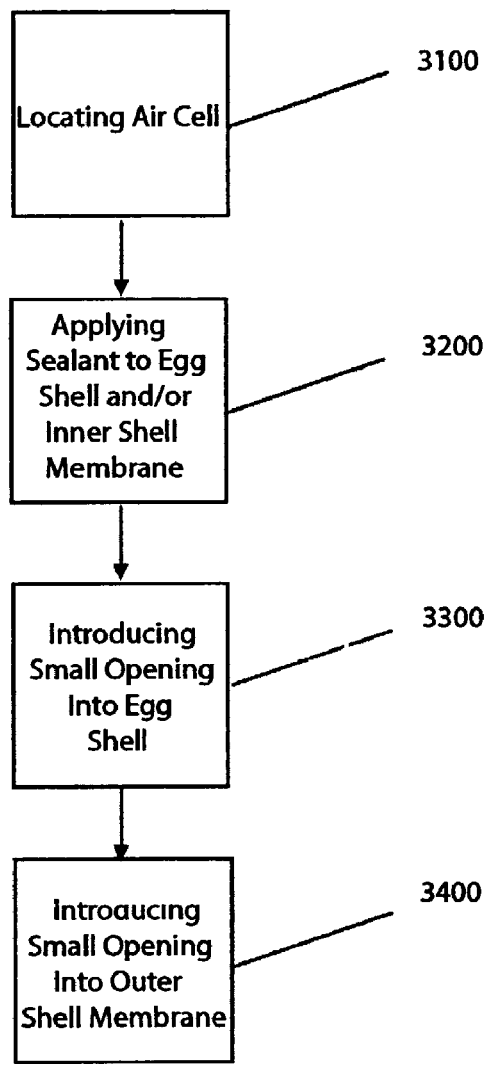
FIG. 4 is a flow chart that illustrates methods of introducing an opening into an egg according to embodiments of the present invention.

Turning to FIG. 4, a small opening is introduced into the egg shell 3300 and the outer shell membrane 3400. While these steps may be carried out separately, they may also be carried out essentially concurrently, particularly in automated or semi-automated methods. As further optional steps, the position of the air cell at the blunt end of the egg may be determined 3100, typically prior to introducing the opening in the egg shell. As a further optional step, a sealant may be applied to the egg shell 3200 prior to or after making a small opening therein, so that the opening in the egg shell will be essentially self-sealing. Alternatively, or additionally, a sealant may be applied to the inner shell membrane prior to or after piercing the inner shell membrane with the device.

Figure 5:
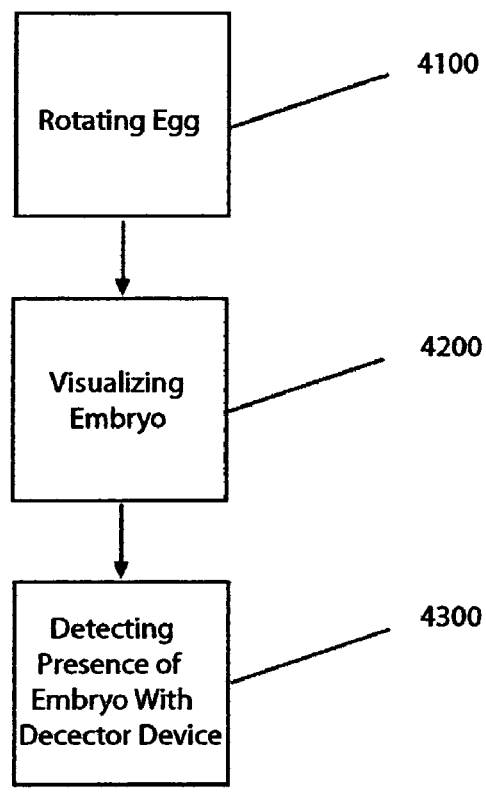
FIG. 5 is a flow chart that illustrates methods of determining the location of an embryo prior to injection according to embodiments of the present invention.
Figure 6:
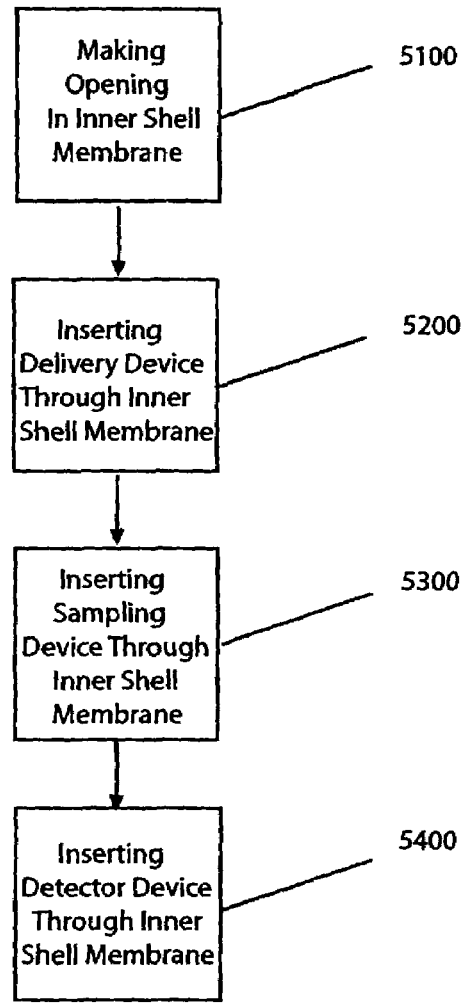
FIG. 6 is a flow chart that illustrates methods of inserting a device into an egg according to embodiments of the present invention. The device may be, for example, a delivery device, a sampling device, or a detector device, or a combination of the foregoing.

In some embodiments of the invention, the device will be inserted into the egg at a predetermined depth and location. In other embodiments, the device will be inserted into the egg based on the position of particular compartments or structures in the egg, e.g., the embryo or the subgerminal cavity within the egg. The position of the embryo or subgerminal cavity may be determined concurrently with or prior to injection (or sampling). Preferred methods of locating the embryo are shown in FIG. 5. For manual or semi-automated injection methods, the embryo may simply be visualized (with or without a magnifying device) 4200 through the window in the egg shell. The egg may further be rotated 4100 to bring the embryo into view. Contrast between the embryo and the background may be enhanced by directing light of particular wavelengths (e.g., blue) on the interior of the egg through the opening in the egg shell or by adding a contrast agent (e.g., a colored or fluorescent dye). Visualization of the early embryo may also be facilitated by feeding a diet or compound to the hen that will affect the color of the yolk (e.g., to a shade of purple or to a different shade of yellow) using techniques known in the art.

In other embodiments, particularly automated or semi-automated injection methods, information regarding the position of the embryo or other compartment within the egg may be detected with a detector device 4300. Detector devices are discussed in detail below, and may be invasive or non-invasive devices. Typically, however, a device will be inserted into the opening in the egg shell and the outer shell membrane to collect information relevant to determining the position of the embryo within the egg. The detecting step may be carried out essentially concurrently with a delivery and/or sampling step. Alternatively, they may be carried out sequentially. Preferred apparatus for concurrent in ovo injection and detection are as described in U.S. Pat. No. 6,244,214 (Hebrank).

As described above, and shown in FIG. 6, the inner shell membrane is maintained in an essentially intact condition (as described above) prior to insertion of a device therethrough. A small opening is made in the inner shell membrane 5100, typically above or in close proximity to the embryo. Typically, the small opening is made by piercing the inner shell membrane by insertion of a device therethrough. The device may be a delivery device 5200, a sampling device 5300, or a detector device 5400. In some embodiments, the device may contain detector, delivery and/or sampling functionalities.

In some embodiments, the steps of introducing an opening into the shell and outer shell membrane and, optionally, piercing the inner shell membrane are carried out concurrently, i.e., in a single step. Typically, however, the opening will be introduced into the egg shell as a separate step because the devices used according to the present invention may be of too narrow a diameter to punch through the egg shell, depending upon the functionality (e.g., a microinjection needle). Likewise, although the invention may be carried out by injecting through the outer and inner shell membranes concurrently (in particular when injecting into the side of the egg, where the membranes are fused), when injecting into the blunt end of the egg, these steps will generally be carried out separately.

The injection methods described herein may be fully manual, fully automated, or semi-automated. For example, the steps of egg preparation and positioning the embryo, as shown in FIG. 1, may be more suited for manual procedures. The steps of introducing the opening in the egg shell and outer shell membrane, locating the embryo and inserting the device, may be manual, but are preferably automated.

In preferred embodiments, a multi-site injection or sampling device is used, for example, as described in U.S. Pat. No. 6,032,612 (Williams et al.). Other preferred delivery or sampling devices include those described in U.S. Pat. No. 5,136,979 (Paul et al.); U.S. Pat. Nos. 4,681,063 and 4,903,635 (Hebrank); and U.S. Pat. Nos. 4,040,388, 4,469,047, and 4,593,646 (Miller).

In a further embodiment, an injection apparatus further comprising a detector as described in U.S. Pat. No. 6,244,214 (Hebrank) is used to collect information regarding the position of the embryo (e.g., blastoderm) or other compartment prior to or concurrently with injection into the egg (for the purposes of sampling and/or delivering a substance into the egg or embryo).

The timing of the detecting step will depend upon the particular purpose of the method or feature being detected, and the nature of the material being injected or the sample being withdrawn. In general, the detecting step may be carried out before, after, or concurrently with a delivering or sampling step.

Electrical sensors, optical sensors, chemical sensors, temperature sensors, acoustic sensors, pressure sensors, or any other device for detecting a physical or chemical parameter may serve as the detection means or detector in carrying out this aspect of the present invention. The detector or sensor may be connected to the outer side-wall of the injection device, or in the case of an electrical detector, and where the device is formed from a conductive metallic material rather than an insulative or polymeric material, the side wall of the injection device itself may serve as the detector, with suitable circuitry connected thereto. The detector could be one or two (or more) electrodes carried by a non-conductive injection device, or carried on an insulated portion of a conductive injection device. It will be appreciated that, for the purpose of sensing depth or location within the egg anatomy, and for a variety of other purposes, numerous different physical or chemical parameters may be sensed or detected, as long as they provide a useful indication of whether or not the egg should be injected, or a useful indication that a particular depth or position has been achieved.

The sensor may be positioned at the tip of the injection device, or at a predetermined position along a sidewall thereof, and/or spaced apart from the tip of the injection device.

Biosensors may be used to carry out the present invention. Numerous biosensors are known. See. e.g., U.S. Pat. Nos. 5,804,453, 5,770,369, 5,496,701, 4,682,895, 5,646,039, 5,587,128, and 4,786,396.

When an electrical detector is used, it may be desirable to provide a second electrode in operative association with a first electrode. Where two electrodes are employed, they may be both connected to the injection device, or one may be connected to the injection device and the other separately inserted through the same opening in the eggshell. In a preferred embodiment, the second electrode is contacted to the exterior of the egg. An electrical signal may be passed through the two electrodes, and the presence or absence of conduction between the two electrodes detected. When the second electrode is simply contacted to the exterior of the egg, the signal is preferably an alternating current signal so that the second electrode is capacitatively coupled to the interior contents of the egg. Preferably each egg (or a flat containing a plurality of eggs) is placed on top of a conductive material prior to detection using an electrical detector (see, e.g., U.S. Pat. No. 5,591,482 regarding conductive polyurethane foam).

When an electrical detector is used to sense the location of a fluid-filled compartment such as the sub-germinal cavity, the electrical detector senses the entry of the probe into the fluid compartment and thus serves as a depth detector (the term "depth detector" encompassing "position detector" herein). In one embodiment of the present invention, the motion of the detector and/or the associated injection device is halted as the detector and/or the device enters the compartment. In this manner an injection device can be halted just after penetrating the subgerminal fluid, but prior to penetrating all the way through the cavity.

An optical sensor may comprise a fiber optic fiber, and may be connected to an external wall portion of the injection device. A light source may be provided through a second fiber optic fiber inserted concomitantly with the device into the egg, or an external source of illumination may be directed at the egg. Light conduction or transmission properties may be used to determine the position of the embryo or the subgerminal cavity. Light may also detect a color marker for a physiological measurement, a disease measurement, or a gender measurement.

A chemical sensor may be provided in any of a variety of manners known to those skilled in the art of biosensors. For example, a chemical sensor, may be provided through BBLO® liposome technology available from Becton Dickinson Microbiology Systems, Cockeysville, Md. USA, or as described in U.S. Pat. Nos. 4,703,017 and 4,743,560. The results of such an assay, when the components are mounted on the injection device, may be determined by reading with a fiber optic fiber as discussed above. Other chemical assays may be performed by electrochemical detection. Such sensors may be used, for example, to determine the position or gender of the embryo within the egg, and to detect potential microbiological infection within the egg.

The chemical sensor may be a pH sensor mounted to the injection device, with the pH measurement being used to detect potential microbial contamination, distinguish live from dead eggs, etc. Ion-specific electrodes to detect various anion or cation species may also be used, as discussed further below. Ion and pH probes sense movement between compartments within an egg by the differences in chemistry of the biological fluids present in the various areas and compartments of an egg.

A temperature sensor may be used to distinguish live from dead eggs or the position of the embryo and/or subgerminal cavity based on the temperature thereof, or for the gender sorting of eggs.

An acoustic sensor can be used as a passive or active sensor (i.e., coupled with an acoustic signal source such as a transducer contacted to the external portion of the egg) to determine depth, to distinguish viable from non-viable eggs, to determine the position of the embryo or subgerminal cavity, etc.

A location or depth sensor can be implemented by any of a variety of techniques. Electrical contact with the air cell membrane can be used to control penetration of the device relative to preselected compartments of the egg, e.g. to a predetermined depth below the air cell membrane, to insure more accurate injection into the subgerminal cavity, into the embryo, or into any other desired location, etc. Alternatively, depth can be sensed with a pressure sensor to assess pressure changes during transition of the device from compartment to compartment within the egg (e.g., air cell to embryo; embryo to subgerminal cavity; etc.). One suitable method of sensing the location of the sensor measures the pressure exerted on the sensor by the egg media surrounding the sensor. For example, the pressure required to emit a gas or liquid into the media surrounding an exit aperture located in the sensor can be measured using either the injection device or a hollow gas or fluid-filled tube. The discharge pressure required increases as the exit aperture moves from a gas-filled compartment (e.g., air cell) into a liquid-filled compartment; and increases again as the exit aperture moves from a liquid-filled compartment into the embryo. Changes in pressure can be measured by a pressure measurement device located outside of the egg.

A light sensor can be used in conjunction with an external light source or a light source carried by the device to distinguish whether the device is in an air-filled compartment such as the air cell, a fluid-filled compartment such as the subgerminal cavity or the yolk, or a cellular compartment such as the embryo.

The sensor may be a diagnostic sensor for the detection of a bacterial contamination or other microbiological contamination of the eggs, such as *Escherichia coli, Salmonella*, or *Listeria monocytogenes* contamination of eggs. The diagnostic sensor may be implemented by any suitable means, typically a chemical sensor or biosensor. Detection of a contaminated egg may be used to trigger a signal for subsequent sorting of the contaminated from uncontaminated eggs.

A plurality of sensors may be associated with the device. For example, where it is desired to detect microbial contamination of the egg, to determine the position of a structure in the egg, or where it is desired to gender sort the egg, it may be beneficial to provide two different or distinct types of data to provide a more accurate indication of the desired condition.

The detection step may be carried out by withdrawing a sample from the egg into a processing system in which subsequent, analysis is carried out. For example, a liquid sample may be withdrawn and analyzed to obtain the desired information therefrom in the same manner as available analytical systems for processing small liquid samples (e.g., in which samples are separated by air gaps in the liquid processing line). In such cases, it is preferable to provide a way to identify the egg from which each biological sample is withdrawn, for example by providing hardware, software, or combinations of hardware and software for counting the eggs and the relative position of each egg, in association with the time of sampling and storing that information for a short or long period of time until it is used in the manner desired (e.g., to reject a particular egg, to sex the birds and sort by gender, or to provide a large database of information about the quality or some other parameter of the eggs injected).

It will be appreciated that the present invention may provide a way to record and store large amounts of information about eggs being injected. For example, population data can be obtained that can be used for quality control programs, or to modify the prior treatment of the eggs, or to modify selective breeding programs. In such cases, the identity of the egg injected may be its association with a particular batch of eggs, rather than its identity as a particular individual within that batch of eggs.

Accordingly, the present invention provides improved methods of manipulating an avian egg containing an early embryo (e.g., blastoderm), and for manipulating the embryo itself. The invention may be used, for example, to collect information from the egg, to remove a sample from the egg, and/or to deliver a substance to the egg.

Having now described the invention, the same will be illustrated with reference to certain examples, which are included herein for illustration purposes only, and which are not intended to be limiting of the invention.

EXAMPLE 1

The following is an exemplary method used to inject fluid or cells into recipient chicken blastoderms in ovo through the blunt end of the egg:

1. Surface sterilize the entire egg surface of Day E 0 eggs by wiping with 100% ethanol.
2. Candle the egg to locate the air cell. The position of the air cell is marked on the shell with a pencil.
3. A window (small opening) is made at the blunt end of the egg (in center of air cell) by dremeling away the shell. Care is taken to keep the outer shell membrane intact.

All of the following steps are preferably carried out in a laminar hood or in a clean room:

4. The blunt end of the egg, where the outer shell membrane is exposed through the window in the shell, and the surrounding area are again surface sterilized using 70% ethanol.
5. The outer shell membrane is carefully removed with forceps and scalpel (#11 blade; Personna Medical) taking care not to leave any jagged edges to the membrane.
6. The blastoderm is visualized beneath the air cell membrane (i.e., inner shell membrane) as the doughnut shaped structure.
7. A glass micropipette (or needle) is used to pierce through the air cell membrane and inject into the subgerminal fluid of the blastoderm. Approximately 3-5 microliters of fluid (containing Penicillin-streptomycin at 100 μg/ml) is injected. Micropipettes were pulled using a Sufter P-30 puller; Temperature—800, Pull-950.
8. Following injection, waterproof tape (Johnson & Johnson, 1 inch wide), cut to fit the window is affixed over and pressed into place.
9. Silicone (GE Silicone II, clear) seal is then spread over entire surface of tape with emphasis on sealing the edges of the tape.
10. Silicone is allowed to dry for approximately 30-45 minutes before eggs are transferred to the incubators.

EXAMPLE 2

A series of experiments was carried out to evaluate the use of manual injection as described in Example 1 to inject either fluid or cells into the subgerminal cavity of recipient chicken blastoderms (approximately Stage X) in ovo. Donor cells were also from Stage X chicken blastoderms. In some cases, the recipient embryo was compromised prior to injection. In early experiments, a small droplet (a few μl) of an albumen solution was deposited on the inner shell membrane above the blastoderm and injection was performed by piercing the membrane through the albumen droplet. In later experiments, this step was omitted. Eggs were either not stored or stored from 4 to 8 days prior to treatment.

Hatch rates in control and manipulated eggs were determined. The rate of successful chimera production was also evaluated. The results are shown below in Table 1.

TABLE 1

| Recipient Egg Breed[a,b] | Compromise Recipient Egg? | Donor Egg Breed | No. of Eggs injected | No. of Cells injected | Hatchability of Control Eggs Recipient | Hatchability of Control Eggs Donor | Hatchability of Injected Eggs | Percent Chimera Obtained Based on no. of eggs set | Percent Chimera Obtained Based on no. of chicks hatched |
|---|---|---|---|---|---|---|---|---|---|
| R X R | No | — | 17 (drop of albumen) | — | 27/30 = 90% | — | 13/17 = 76% | | |
| R X R | No | — | 17 (drop of albumen) | — | 22/30 = 73% | — | 10/17 = 59% | | |
| R X R | No | — | 20 (no fluid) | — | 27/30 = 90% | — | 18/20 = 90% | | |
| R X R | No | — | 21 (no fluid) | — | 30/30 = 100% | — | 15/21 = 71% | | |
| R X R | No | — | 20 (no fluid) | — | 23/25 = 92% | — | 10/20 = 50% | | |
| R X R | No | — | 21 (no fluid) | — | 24/27 = 89% | — | 13/21 = 62% | | |
| R X R | No | — | 20 (no fluid) | — | 21/25 = 84% | — | 9/20 = 45% | | |
| R X R | No | — | 38 (no fluid) | — | 17/20 = 85% | — | 28/38 = 74% | | |
| R X R | No | — | 14 (no fluid) | — | 14/14 = 100% | — | 9/14 = 64% | | |
| R X R | No | BPR | 15 (no fluid) | 625, 1250 | 22/30 = 73% | — | 625:27% 1250:53% | 0% 0% | 0% 0% |
| R x R | No | BPR | 30 (no fluid) | 500, 1000 | 80% | 53% | 500:47% 1000:40% | 0% 0% | 0% 0% |
| R x R | Yes | BPR | 20 (no fluid) | 500, 1000 | 78% | — | 500:60% 1000:60% | 10% (1/10) 0% | 16% (1/6) 0% |
| R x R | Yes | BPR | 20 (no fluid) | 500, 1000 | 64% | — | 500:50% 1000:10% | 0% 0% | 0% 0% |
| R x R | Yes | BPR | 24 | 500, 1000 | 47% (compromised) | — | 500:17% 1000:33% | 8.3% (2/12) 0% | 50% (1/2) 0% |
| HyVac (SPF) | Yes | BPR | 25 | 500, 1000 | 70% (compromised) | 57% | 500:63% 1000:58% | 7.6% (1/13) 16.6% (2/12) | 12.5% (1/8) 28.5% (2/7) |
| R x R | Yes | BPR | 25 | 1000 | 80% 64% (compromised) | 76% | 60% | 8% (2/25) | 13.3% (2/15) |
| R x R | No | BPR | 39 | 1000 | 87% | 69% | 62% | 10% (4/39) | 16.6% (4/24) |
| R x R | No | BPR | 30 | 1000 | 97% | 20% | 57% | 0% | 0% |
| BPR | No | R X R | 35 | 1000 | 11% | 89% | 63% | 14.2% (5/35) | 22.7% (5/22) |
| Bovans | No | BPR | 50 | 1000 | 78% | 72% | 68% | 6% (3/50) | 9% (3/34) |
| Bovans | Yes | BPR | 30 | 1000 | | | 70% | 0% | 0% |
| Bovans | Yes | BPR | 20 | 1000 | 75% 80% (compromised) | 60% | 75% | 0% | 0% |
| Bovans | Yes - for one treatment group | BPR | 15 | 1000 | 87% 13% (compromised) | 47% | 73% (not compromised) 7% (compromised) | 6.6% (1/15) | 100% (1/1) |

[a]Abbreviations: RxR = Rhode Island Red Cross; BPR = Barred Plymouth
[b]HyVac and Bovans are strains of Leghorn chicken.

EXAMPLE 3

Figure 7:
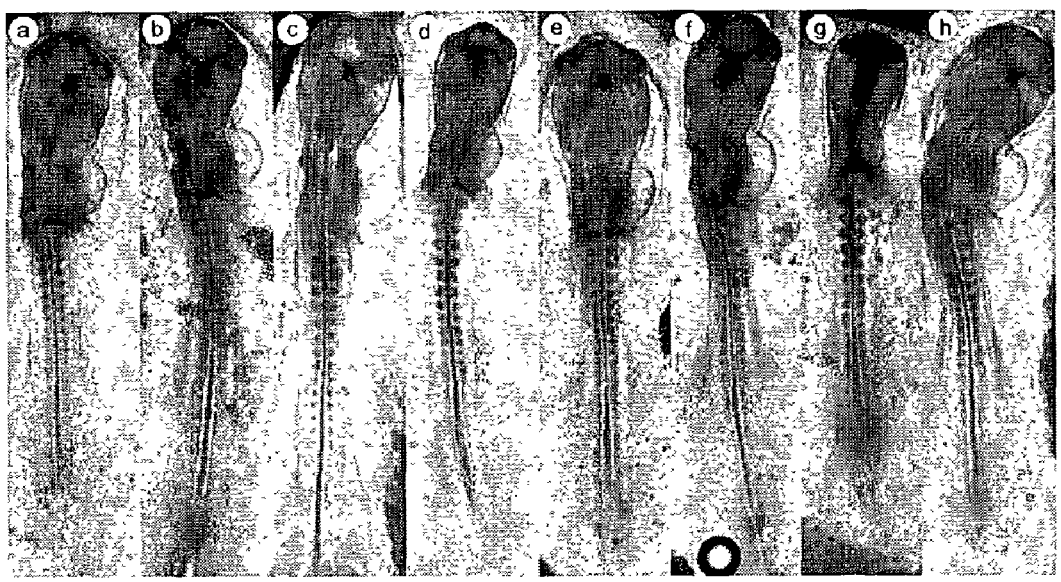
FIG. 7 shows photographs of two-day old embryos from windowed eggs. Panels: (a) Representative control embryo, from a non-windowed egg. (b-h) Experimental embryos, from windowed eggs. Experimental embryos are virtually identical in stage and morphology as compared with controls.

Certain methods of physical compromise of the embryo, such as ultraviolet (UV)-irradiation or laser ablation, may be administered through a window in the egg shell and shell membranes. We have developed a method to create a window in the side of the egg, seal it, and incubate the egg under standard conditions (99 F, rocking), that allows a very high percentage (>90%) of embryos to develop normally at two days (FIG. 7). This method may be used to evaluate the effects of compromise and chimera production at two days of embryonic development. Further, this method may be used to inject into the side of the egg.

Briefly, the eggs were treated as follows:
1. Eggs were stored at 60 F, 75% humidity for 0-7 days, on their long axis, to steer the blastoderm towards the center of the side of the egg.
2. The position facing upwards was marked with a sharpie pen.
3. Following storage, a 7-mm hole was drilled at the side of the egg, at the location of the pen mark.
4. The shell was removed. Usually, the inner and outer shell membrane remained intact, and those were also removed.
5. The blastoderm was identified, near or directly underneath the opening made in the egg shell. For this particular experiment, only those eggs were used where the blastoderm was directly underneath the opening, allowing application of various compromise treatments, such as UV-light.
6. The hole was left open for 5-10 minutes.
7. The hole was sealed with GE Silicon II and J&J waterproof tape.

8. The silicon was allowed to dry for about 30 minutes.
9. Eggs were placed in an incubator with the blunt end up, hole on the side, and incubated at 99 F with turning every 3 hours, for two days.
10. Embryos were collected from the eggs for photography.

Photographs of representative control and treated embryos are shown in FIG. 7.

EXAMPLE 4

A method of monitoring blastodermal cell incorporation into recipient embryos was developed. This method is applicable to tracing freshly isolated blastodermal cells from any avian species or strain, and should be easily applicable to monitoring the incorporation of other cell, such as embryonic stem cells. To summarize the method, freshly isolated blastodermal cells were exposed to carboxyfluorescein-diacetate-succinyl-ester (CFDA SE) prior to injection. CFDA SE is an amine-reactive compound, which becomes highly fluorescent upon reacting with intracellular proteins. Once it is incorporated into blastodermal cells, those cells can be monitored in a recipient embryo by fluorescence microscopy.

Figure 8:
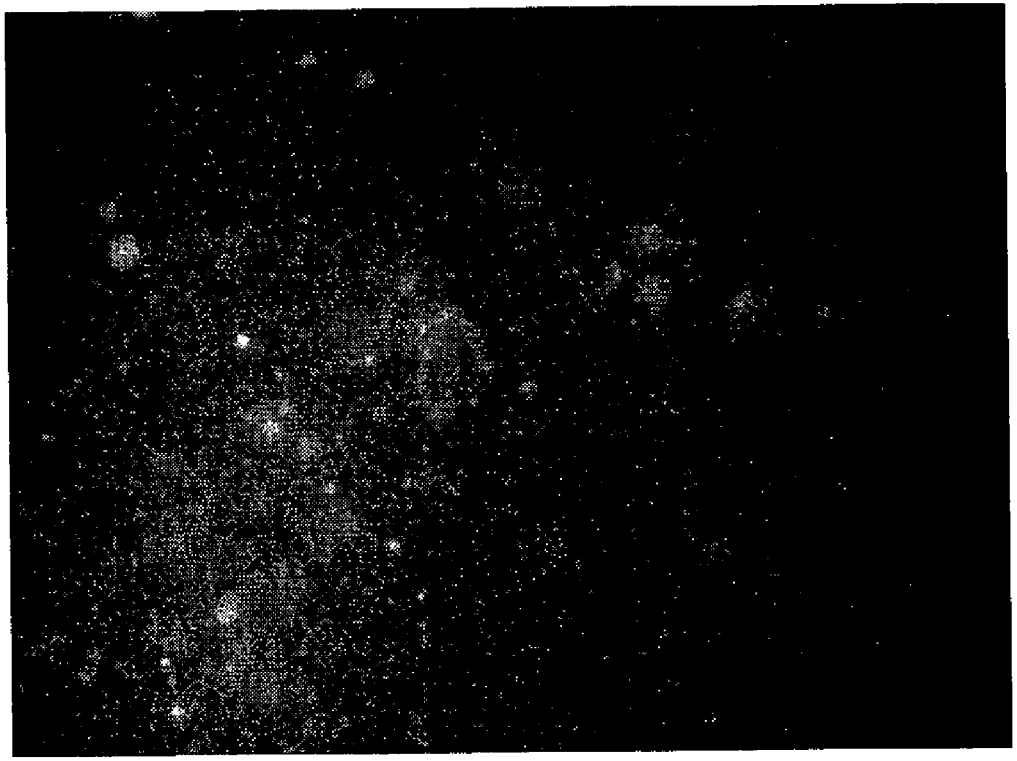
FIG. 8 shows detection of fluorescently labeled cells (green) in the somite of a 2-day incubated recipient embryo.

In the experiment illustrated below, freshly isolated blastodermal cells were labeled with CFDA SE and microinjected into Stage X blastoderms, by injection through the inner-shell membrane at the blunt end of the egg (as described in Example 1). When observed by microscopy after two days of incubation, fluorescently labeled donor cells were found in a variety of tissues. FIG. 8 shows fluorescently labeled donor cells incorporated into the somite of a 2-day incubated recipient embryo to create a chimeric embryo. Fluorescent dye labeling may be an attractive alternative or complement to using genetically modified cells to follow donor cell incorporation in early embryos.

EXAMPLE 5

In order to optimize chick chimera production, recipient embryos may be 'compromised' or preconditioned so that they are more receptive to the donor cells. The most widely accepted of method of compromise involves exposing recipient eggs to 600 rads of gamma-irradiation. In order to assess the effects of various treatments on recipient embryos, we have developed techniques to measure the amount of cell death in situ in the recipient blastoderm.

To identify necrotic cells in situ, we have assessed dye-labeling with Propidium Iodide (PI), a fluorescent DNA stain which is primarily permeable to dead cells. It was found that with a minimum amount of handling and washing the delicate blastoderm, PI effectively labeled necrotic cells. These cells can be identified and photographed by fluorescence microscopy, and the relative amount of cell death determined by digital image analysis (see FIG. 9). The precise location of necrotic cells in the blastoderm can also be determined by digital image analysis (see FIG. 9). To our knowledge, this is the first time that cell death has been measured in situ in a living avian embryo.

Figure 9:
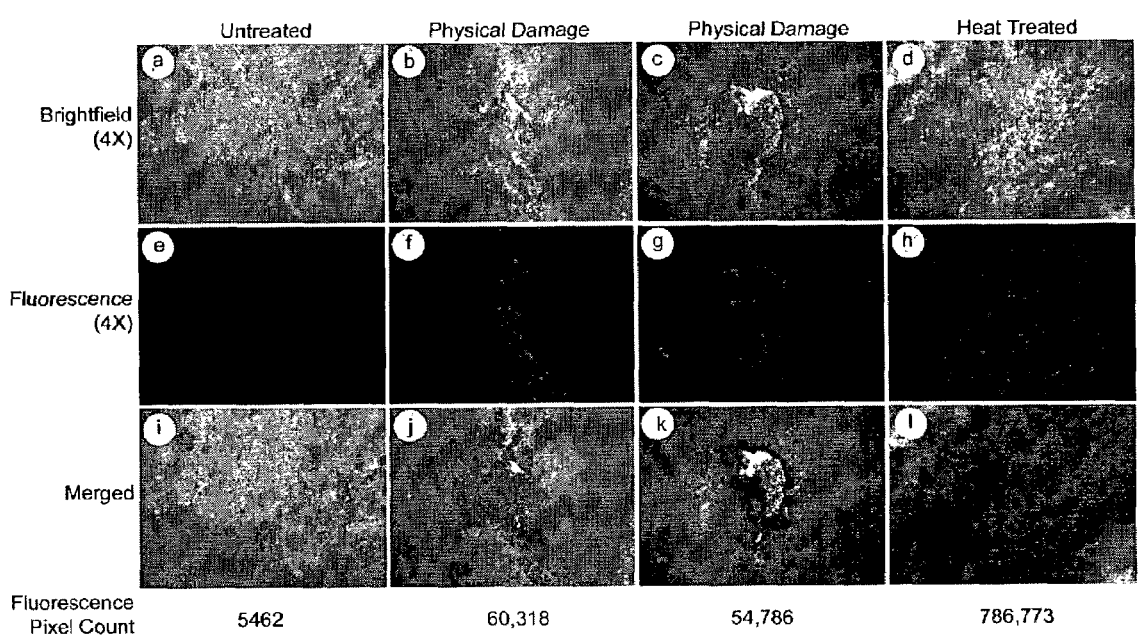
FIG. 9 represents a series of photomicrographs showing in situ identification of cell death in stage X avian embryos. All pictures shown are from the central region of the area pellucida of stage X chick embryos. Embryos shown in the top row (panels a-d) are photographed under brightfield-lighting and the middle row (panels e-h) shows the same fields photographed under epifluorescence illumination using a rhodamine filter-set. The bottom row (panels i-l) shows the top two rows digitally merged, to demonstrate the precise localization of cell death in the blastoderm. The Fluorescence Pixel Counts (bottom row) indicates the number of red pixels from the digitized fluorescence image, allowing quantitative comparison of the amount of cell death.

In this experiment, the PI labeling technique was applied to untreated, physically damaged, and heat-treated embryos. The untreated blastoderm (FIG. 9, first column) shows the low level background cell death. The physical damage inflicted in this experiment (second and third columns) was unintended damage caused by the blastoderm isolation procedure. Note that the cell death can be precisely localized to areas surrounding tears in the blastoderm (FIG. 9, panels j and k). The heat treatment (55 C for 15 minutes in a water bath) was based on previous data indicating that this treatment completely eliminates hatch. As shown in this experiment (FIG. 9, fourth column), this reduction in hatch is likely due to the extremely high level of cell death in the blastoderm. The fluorescence pixel counts (FIG. 9, bottom row) can be used to quantitatively measure and compare the amount of cell death between treatments.

Detection of apoptotic cells (as opposed to necrotic cells) may also be determined using the fluorescent dye Hoechst 333342, which differentially stains living and apoptotic cells. Measurement of apoptotic and/or necrotic cells may be used to determine the extent of compromise of the recipient embryo.

EXAMPLE 6

The following studies were carried out to determine the position and diameter of the blastoderm in eggs stored under commercial hatchery storage conditions. White leghorn eggs (Bovans) from a single flock are measured on a weekly basis; the flock is studied to the end of its laying cycle. Eggs are received within 24 hours of lay. After the eggs are received, they are stored for 6 or 7 days at 60 F, and 75% relative humidity, in flats, similar to the way they are stored in commercial hatcheries. Fifty eggs in flats are measured each week. The average off-center distance of the blastoderm is 5.24 mm for eggs stored for 6 or 7 days in flats, with 3.05% of the embryos too far off-center to be seen.

In addition, a Hy-Line W-36 White Leghorn flock is studied. These eggs are received up to 48 hours after lay. The eggs are stored for 6 or 7 days at 60 F and 75% relative humidity. The average off-center distance of the blastoderm is 5.86 mm for eggs stored for 6 or 7 days in flats with 3.96% of the embryos too far off-center to be seen.

The diameter of the blastoderm, including the diameter of the area pellucida, is also measured at the time blastoderm position is measured. The results are shown in Table 2 below under commercial hatchery storage conditions. The eggs were stored for 7 days, and the embryos were typically seen as Stage X embryos.

TABLE 2

| Flock | No. of Eggs Measured | Diameter Area Pellucida (mm) | | Diameter Area Opaca (mm) | |
|---|---|---|---|---|---|
| | | Average | Std. Dev. | Average | Std. Dev. |
| Bovan | 2146 | 1.99 | 0.26 | 3.68 | 0.36 |
| Hy-Line | 1351 | 2.11 | 0.25 | 3.87 | 0.36 |

EXAMPLE 7

Experiments were carried out to determine whether the blastoderm may be passively steered by modulating storage conditions. The eggs were stored either in flats as under commercial conditions (controls) or in a device called a "fixture" that holds the eggs in a fixed upright position (blunt end up) where both side-to-side movement and rotation around the vertical axis of the egg were essentially prevented.

In an ongoing study with a Bovan flock (the hens were in their $69^{th}$ week of lay; they lay up to 70 weeks approximately, without a molt), a total of 2,766 eggs stored either in flats or in a fixture for 7 days, at 60 F and 75% RH (30 eggs stored in flats and 30 eggs stored in fixtures, weekly for 31 weeks), were measured on an Acu-Gage optical Coordinate Measuring Machine (CMM) with a blue fiber-optic light source to enhance the contrast of the blastoderm. Based on the collected data, the average off-center distance of the blastoderm was 5.24 mm for eggs stored for 7 days in flats.

The off-center distance improves to an average 4.58 mm for the eggs stored for 7 days in a fixture device that holds the eggs such that the long axis of the egg is vertical. In eggs stored in flats, 3.05% of the embryos were too far off-center to be seen, while in eggs stored in fixtures only 2.53% were too far off-center. Hy-Line W-36 eggs from Elizabethtown, Pa. were also measured. A total of 1,649 eggs were measured, where the eggs were stored for 6 or 7 days at 60 F and 75% relative humidity. The average off-center distance of the blastoderm was 5.86 mm for eggs stored for 6 or 7 days in flats with 3.96% of the embryos too far off-center to be seen. The off-center distance for the eggs stored for 6 or 7 days in fixtures such that the long axis of the egg was vertical was slightly better, an average 5.31 mm, and 4.81% of the embryos were too far off-center to be seen.

Statistical analysis on the data (Bovans, 23-69 weeks; Hy-Line, 26-42 weeks) was performed to determine whether holding the egg in the fixture device influenced the position of the blastoderm. Data from infertile or damaged eggs were excluded. If the blastoderm was too far from the center to be measured, a value of 13.716 was applied. An analysis of covariance was utilized that considered position as the dependent variable and storage device (in a fixture or in an egg flat) as fixed, with analyses conducted separately by breed. The effect of storage in a fixture as compared with flats on blastoderm position pooled across flock ages is presented in Table 3 below.

TABLE 3

|  |  | Blastoderm Position off-center (mm) | |
| --- | --- | --- | --- |
|  |  | Bovans | Hy-Line |
| Flat | Mean | 5.5370 | 6.2241 |
|  | SD | 3.1126 | 3.2125 |
|  | N | 1085 | 729 |
| Fixture | Mean | 4.9579 | 5.7333 |
|  | SD | 3.0161 | 3.2439 |
|  | N | 1257 | 736 |

The effect of storage in a fixture was significant for both the Bovans ($p<0.001$) and the Hy-Lines ($p<0.004$); eggs stored in fixtures resulted in blastoderms significantly closer to the center.

The dataset of eggs stored in a fixture was analyzed to determine whether blastoderm position off-center was correlated with flock age and/or egg weight. An analysis of covariance was performed that considered position as the dependent variable and flock age fixed, with egg weight as covariate. The analysis was separated by breed. Bovans eggs show a highly significant ($p \leq 0.001$) flock age effect for eggs stored in fixtures, while Hy-Line eggs did not show any significant correlation between blastoderm position with flock age ($p \geq 0.05$).

As expected, egg weight increased with flock age; an inverse relationship was observed between egg weight and blastoderm distance from the egg center. The Bovan data set showed egg weight as a significant ($p \leq 0.05$) covariate; while egg weight was not a significant co-variate for the Hy-Line eggs (data not shown). It may be that egg weight is not a significant covariate in the Hy-Line analysis because the flock age did not exceed 42 weeks of age and, thus, egg weight may not as yet be a factor. While regression analysis of the Bovan dataset showed a significant relationship between egg weight and blastoderm position, it indicated that less than 1% of the variation in blastoderm position could be explained by egg weight ($R^2=0.007$).

The control group for the above experiments was made up of eggs stored in flats. These are cardboard flats in which the eggs are shipped; the eggs can move relatively freely about the vertical axis while held in the flats. Hatcheries use plastic flats, in which the egg has only a restricted level of movement about the vertical axis. To determine the effect of storing eggs in plastic flats versus cardboard flats or in fixtures, Bovan eggs were stored in either plastic or cardboard flats as well as in fixtures for 6 days at 60 F, 75% RH. As shown in Table 4 below, blastoderm position off-center was reduced in eggs stored in plastic flats, but were much improved in eggs stored in fixtures.

TABLE 4

| Storage Vessel |  | Blastoderm position off-center (mm) | Blastoderms too far off-center |
| --- | --- | --- | --- |
| Cardboard Flats | Mean | 6.586 | 8% |
|  | SD | 3.460 |  |
|  | n | 45 |  |
| Plastic Flats | Mean | 5.442 | 4% |
|  | SD | 2.947 |  |
|  | n | 47 |  |

EXAMPLE 8

Studies were carried out to determine the effect of different storage time periods on blastoderm position. A previous study demonstrated that eggs stored for 7 days (at 60 F and 75% relative humidity) showed a significant improvement in the position of the blastoderm (from 9.71 mm off-center on day 0 to 5.61 mm off-center on day 7, significant at 0.0001 level) over day 0 eggs, and storing eggs for 10 days did not significantly improve blastoderm position any further.

One of the variables believed to affect blastoderm position is albumen thickness; a thicker albumen restricts the free rotation of the yolk. Albumen thickness is measured in terms of Haugh units. In a separate experiment, albumen thickness was measured in eggs stored for various lengths of time. Bovan eggs from a 55-week-old flock were weighed and Haugh units determined after storage in flats for 0, 3, 6, 10, 13, or 17 days. Albumen height or Haugh units were shown to significantly decrease as storage time increased.

An experiment was done to determine the effect of storage time on blastoderm position off-center as well as albumen thickness. Hyline eggs from a 37-week-old flock were weighed and stored in fixtures (blunt end up) for 2, 6, 9, 12, or 15 days at 60 F and 75% relative humidity. The group stored for 6 days was designated the control group. Analyses of covariance that considered blastoderm position as the dependent variable, and storage time (days) as fixed was performed. Separately, Haugh units were considered as the dependant variable and storage time the fixed variable. Mean blastoderm position or mean Haugh units for each storage time were then compared by SNK test. As shown in Table 5 below, blastoderm position off-center significantly decreased as storage time increased, with the mean position for 12 days and 15 days significantly lower than 2 days, with 6 days and 9 days intermediate (the mean position for 6 was actually lower than 9, and 12 lower than 15). Further, Haugh units also significantly decreased with storage time, showing an even clearer effect than blastoderm position.

TABLE 5

|  |  | Storage Time (days) | | | | |
| --- | --- | --- | --- | --- | --- | --- |
|  |  | 2 | 6 | 9 | 12 | 15 |
| No. of eggs |  | 47 | 46 | 45 | 47 | 44 |
| Blastoderm Position off-center (mm) | Mean | 6.6691 | 5.3541 | 5.6500 | 4.4831 | 4.7582 |
|  | SD | 2.9971 | 3.2487 | 3.9817 | 2.9454 | 2.9254 |
| Haugh Units | Mean | 73.8645 | 69.3088 | 66.8423 | 64.0056 | 61.8017 |
|  | SD | 5.2358 | 6.2709 | 8.9072 | 7.0988 | 6.1042 |

Overall, it appears that thinning the albumen allows more freedom of rotation of the yolk and thereby positioning of the blastoderm closer to the "top dead center" of an egg held in a vertical, blunt end up, position.

EXAMPLE 9

Investigations were also carried out to determine the effect of modulating egg orientation during storage on blastoderm position. Preliminary experiments in which eggs were stored on their side for 7 days did not improve blastoderm positioning. However, these experiments had been performed by placing the eggs on a flat surface and allowing them to freely orient themselves in a sideways orientation.

In the present study, eggs were stored in various positions while held in fixtures as described in Example 7, which limited side-to-side and rotational movement to determine the effect on blastoderm position. The fixtures held the eggs in a fixed horizontal or vertical position. The various orientations in which the eggs were stored, as well as the orientation in which the egg was held for the measurement of the blastoderm position, were as follows:
1. Sideways (Bovan and Hy-Line W-36), and measured sideways
2. Upside down (i.e. blunt side down) for three days (Hy-Line W-36), followed by blunt-end up for 3-4 days, and measured blunt end up.
3. Upside down (i.e. blunt side down) for 6-7 days and measured at the blunt end (Bovan).
4. Upside down (i.e. blunt side down) for 6-7 days and measured upside down (Hy-Line W-36).

The results are summarized in Table 6.

TABLE 6

| Storage Condition |  | Blastoderm Position (mm) | % blastoderms too far off | Comments |
| --- | --- | --- | --- | --- |
| 1 Sideways and measured sideways BOVANS | Mean SD n | 3.937 3.441 45 | 6% | Effect of sideways storage of eggs on blastoderm position is not significant. |
| Blunt end up, measured blunt end up | Mean SD n | 4.312 2.540 42 | 2% |  |
| Sideways and measured sideways HYLINE | Mean SD n | 4.783 3.709 47 | 10% | Effect of sideways storage of eggs on blastoderm position is not significant. |
| Blunt end up, measured blunt end up | Mean SD n | 5.213 3.829 45 | 4% |  |

TABLE 6-continued

| Storage Condition |  | Blastoderm Position (mm) | % blastoderms too far off | Comments |
| --- | --- | --- | --- | --- |
| 2 Upside down for 3 days and blunt end up remaining, measured blunt end HYLINE | Mean SD n | 6.258 2.801 40 | 6.5% | Effect of sideways storage of eggs on blastoderm position is significant at 0.057 level. |
| Blunt end up, measured blunt end up | Mean SD n | 5.003 2.997 40 | 2.5% |  |
| 3 Upside down and measured right side up i.e blunt end BOVAN | Mean SD n | 11.451 4.140 47 | 70% | Effect of upside down storage is significant to 0.001 level. |
| Blunt end up, measured blunt end up | Mean SD n | 4.278 2.511 47 | 2% |  |
| 4 Upside down, measured upside down HYLINE | Mean SD n | 12.092 3.798 49 | 82% | Effect of upside down storage is significant to 0.001 level. |
| Blunt end up |  | 5.376 2.845 43 | 2% |  |

Storage of eggs sideways did not produce significantly improved results for either type of egg; although blastoderm distance decreased, the number of blastoderms too far from the center also increased. Storage of eggs upside down for 3 days approached significance but actually increased blastoderm distance from the center of the egg ($p \leq 0.057$). Storage of eggs upside down measured either right side up or upside down resulted in a significant difference, but greatly increased blastoderm distance from the center of the egg, for both Bovan and Hy-Line W-36.

EXAMPLE 10

The effects of storage temperature and relative humidity on blastoderm position were also investigated. Temperature is believed to be an important factor that affects albumen quality (i.e. thickness), which in turn may affect the movement or mobility of the yolk and hence the location of the blastoderm. Preliminary experiments indicated that storing eggs at higher temperatures might help "steer" the blastoderm towards the center of the surface of the yolk.

Hyline eggs from a 47-week-old flock were stored for 7 days at either 60 (commercial hatchery conditions) or 70 degrees F. (15.5 or 21.1 degrees C.). Blastoderm position off-center of eggs stored at 70 degrees were lower than those of eggs stored at 60 degrees (approached significance at $p=0.063$).

In a follow-up study, various permutations of temperature and relative humidity conditions during egg storage were studied for their influence on blastoderm position. Eggs stored in fixtures as described in Example 7 for 6-7 days were subjected to varying combinations of temperature and relative humidity, with 60 degrees F. and 75% relative humidity considered the control treatment. The following different treatment conditions were evaluated:

1. Normal temperature (60 F) with relative humidity (75%) lowered to 50% (Hy-Line W-36 eggs).
2. Normal temperature (60 F) and relative humidity (75%) for first 5 days. followed by increased temperature of 80 degrees (75% RH) for the last two days of storage (Bovan).
3. Normal temperature (60 F) but relative humidity set to 90% (Hy-Line W-36).
4. Temperature set to 70 F and relative humidity set to 50% (Hy-Line W-36).
5. Temperature set to 70 F and normal relative humidity (Hy-Line W-36).
6. Temperature set to 70 F and relative humidity set to 90% (Bovan and Hy-Line W-36).
7. Temperature set to 80 F with normal relative humidity (Hy-Line W-36).

The data analysis is summarized in Table 7 below:

TABLE 7

| | Storage Condition | | | Blastoderm Position (mm) | Haugh Units | Comments |
|---|---|---|---|---|---|---|
| 1 | 60 F; 50% RH | | Mean | 5.1306 | 71.33 | Main effect of RH on blastoderm |
| | | | SD | 2.5212 | 5.21 | position is not significant. |
| | | | n | 45 | 45 | |
| | 60 F, 75% RH (control) | | Mean | 5.2447 | 72.22 | Effect of RH on albumen thickness is |
| | | | SD | 2.8391 | 5.74 | also not significant |
| | | | n | 43 | 43 | |
| 2 | Last two days of storage at | | Mean | 3.2724 | 62.08 | Main effect of temperature on |
| | 80 F, 75% RH | | SD | 1.7535 | 8.59 | blastoderm position is not significant. |
| | | | n | 48 | 48 | |
| | 60 F, 75% RH - all days | | Mean | 3.6235 | 66.73 | Effect of temperature on albumen |
| | (control) | | SD | 2.3655 | 8.30 | thickness significant ($p \leq 0.01$) |
| | | | n | 47 | 47 | |
| 3 | 60 F; 90% RH | | Mean | 5.3228 | — | Main effect of Relative Humidity on |
| | | | SD | 2.7827 | — | blastoderm position is not significant |
| | | | n | 50 | — | |
| | 60 F; 75% RH (Control) | | Mean | 5.7364 | — | |
| | | | SD | 3.1812 | — | |
| | | | n | 49 | — | |
| 4 | 70 F; 50% RH | | Mean | 4.8390 | 69.58 | Main effect of temperature and relative |
| | | | SD | 2.1712 | 5.30 | humidity on blastoderm position is |
| | | | n | 46 | 46 | significant to 0.04 level |
| | 60 F, 75% RH (control) | | Mean | 6.0275 | 71.89 | Effect of temperature and relative |
| | | | SD | 3.1089 | 4.64 | humidity on albumen thickness is |
| | | | n | 48 | 48 | significant ($p \leq 0.05$). |
| 5 | 70 F, 75% RH | | Mean | 4.4427 | 69.83 | Main effect of temperature on |
| | | | SD | 2.6986 | 3.81 | blastoderm position is significant to 0.02 |
| | | | n | 49 | 49 | level |
| | 60 F, 75% RH (control) | | Mean | 5.8881 | 75.34 | Effect of temperature on albumen |
| | | | SD | 3.0702 | 5.53 | thickness is significant ($p \leq 0.001$). |
| | | | n | 48 | 48 | |
| 6 | 70 F; 90% RH | | Mean | 3.5412 | 65.19 | Main effect of temperature and relative |
| | | | SD | 2.5177 | 6.20 | humidity on blastoderm position is |
| | | | n | 48 | 48 | significant to 0.05 level |
| | BOVANS | | | | | |
| | 60 F; 75% RH (control) | | Mean | 4.6323 | 68.22 | Effect of temperature and relative |
| | | | SD | 2.5991 | 7.38 | humidity on albumen thickness is |
| | | | n | 44 | 44 | significant ($p \leq 0.05$). |
| | 70 F; 90% RH | | Mean | 5.6043 | 65.31 | Main effect of temperature and relative |
| | | | SD | 3.6825 | 6.72 | humidity on blastoderm position is not |
| | | | n | 47 | 47 | significant. |
| | HY-LINE | | | | | |
| | 60 F, 75% RH (control) | | Mean | 5.9906 | 72.50 | Effect of temperature and relative |
| | | | SD | 3.0451 | 5.88 | humidity on albumen thickness is |
| | | | n | 47 | 47 | significant ($p \leq 0.001$). |
| 7 | 80 F, 75% | | Mean | 4.7258 | 55.42 | Main effect of temperature on |
| | | | SD | 2.8704 | 7.39 | blastoderm position is significant at |
| | | | n | 40 | 40 | 0.065 level. |
| | 60 F, 75% RH (control) | | Mean | 5.9530 | 69.16 | Effect of temperature on albumen |
| | | | SD | 3.1971 | 7.24 | thickness is significant ($p \leq 0.001$). |
| | | | n | 47 | 47 | |

In summary, a temperature of 70 F appeared in all cases to improve blastoderm positioning and was significant to $p \leq 0.05$ for all cases except for Hy-Line W-36 eggs at 90% relative humidity. Relative humidity changes alone appeared to have little effect on blastoderm position (note that in all cases regardless of significance the control group had increased blastoderm distance from center). Results were similar with Haugh units, which decreased for all treatment groups as compared with the control conditions (note that Haugh unit data was not collected for the normal temperature and 90% relative humidity study). The Haugh unit data showed more significance than the blastoderm position data, with only the normal temperature and 50% relative humidity group not showing a significant effect.

EXAMPLE 11

Modulating the external environment is one method to influence blastoderm position. Exposure of eggs to ammonia has been shown to thin the albumen. Benton and Brake (2000) have shown that eggs exposed to high levels of $NH_3$ (2747 and 6052 mg/kg) for 1 hour show significant reduction in the albumen height with a concomitant increase in albumen pH when compared with the controls (0 mg/kg $NH_3$). Since a reduction in the albumen height has been positively correlated to more fluidity of the albumen, it was $NH_3$ treatment to steer the blastoderm closer to the center of the egg was assessed.

In the first experiment, eggs from 38 week-old Hyline birds (egg type W 36; Flock I.D: PL 2506) were received and maintained for 1 day at 60° F. and 75% RH. Eighteen eggs (three batches for a total of 54 eggs) were placed on their horizontal axis on a porcelain plate in glass desiccators (250 mm in diameter, with caps) (Fisher Scientific). One liter of $NH_4OH$ solution (14.8 M) (Sigma) or double distilled water (control) was poured into the desiccators. The 14.8 M $NH_4OH$ is estimated to release 6052 mg/kg of $NH_3$ (Benton and Brake, 2000). The eggs were exposed for 1 hour to the respective levels of $NH_3$. The eggs were then removed, and the blastoderm position, albumen height and pH were measured. These results are presented in Table 8:

TABLE 8

| Treatment | | PH | Blastoderm Position (mm) | Haugh Units |
|---|---|---|---|---|
| $NH_3$ 6052 mg/kg for 1 hour | Mean | 10.29 | 7.91 | 69.51 |
| | SD | 0.50 | 4.02 | 6.47 |
| | n | 42 | 42 | 42 |
| No treatment | Mean | 9.23 | 7.72 | 74.98 |
| | SD | 0.27 | 4.02 | 5.84 |
| | n | 44 | 44 | 44 |

The results indicate that $NH_3$ treatment caused a significant increase in albumen pH when compared with their respective controls. The albumen height in the $NH_3$ treated group was lower (i.e., had lower Haugh unit values) indicating a thinning of the albumen.

In another experiment, the eggs were stored after exposure to ammonia. The eggs (68-week-old Bovans) were subjected to two concentrations of $NH_3$ (2747 and 142 mg/kg of $NH_3$). The controls were exposed to 0 mg/kg of $NH_3$. A total of 50 eggs were used for the $NH_3$ treatments and 48 eggs were used for the control. Serial dilutions of one liter of $NH_4OH$ solution (14.8 M) (Sigma) were done to give 2747 or 142 mg/kg of $NH_3$. For the controls, double distilled water (1 L) was poured into the desiccators. The eggs were exposed for 1 hour to the respective levels of $NH_3$. The eggs were then removed, placed in fixtures with no rotational or side-to-side movement, and stored at 60 F and 75% RH for 6 days. After the 6-day storage, measurements were carried out to determine the blastoderm position, albumen height and pH. The results are shown in Table 9 below:

TABLE 9

| Treatment | | PH | Blastoderm Position (mm) | Haugh Units |
|---|---|---|---|---|
| $NH_3$ 2747 mg/kg treatment for 1 hour | Mean | 9.02 | 4.16 | 64.00 |
| | SD | 0.11 | 2.72 | 9.56 |
| | n | 45 | 45 | 45 |
| $NH_3$ 142 mg/kg treatment for 1 hour | Mean | 9.05 | 6.50 | 69.11 |
| | SD | 0.07 | 2.79 | 8.74 |
| | n | 40 | 40 | 40 |
| None (control) | Mean | 9.04 | 5.19 | 67.72 |
| | SD | 0.07 | 3.15 | 7.57 |
| | n | 36 | 36 | 36 |

The blastoderm position off-center in the eggs treated with 2747 mg/kg of $NH_3$ is much closer to the top dead center of the blunt end of the egg as compared with the controls. Interestingly, the pH of these eggs is similar to the control. There were no differences in the Haugh Units among the $NH_3$-treated and control eggs. The lower concentration of $NH_3$ (142 mg/kg) showed no changes in any of the measured parameters as compared with the controls.

One of the changes that was observed with the embryos at the 2747 mg/kg $NH_3$-treated groups is that they had a "cooked" appearance and did not look alive. Thus, treatment with high levels of ammonia may be useful as a method of compromising the embryo.

EXAMPLE 12

A variety of approaches were evaluated to determine whether the blastoderm could be actively "steered" to the center of the egg.

Centrifugation.

Gravity is believed to play an important role in orienting the blastoderm in the uppermost position in the egg. Centrifugation is a way to create an artificial gravity or increase the body force of gravity. Studies were conducted to determine whether the greater force due to centrifugation would improve the position of the blastoderm.

Hyline eggs from 27-week-old flocks were weighed, placed in fixtures as described in Example 7, and stored for a total of seven days. On day five of storage, the eggs were placed in Sorval RC 5C centrifuge buckets and spun for 3 minutes at 500 rpm while held in fixtures with the long axis of the egg aligned with the artificial gravitational force throughout the spin. The eggs were then stored for two more days, and then the position of the blastoderm from the egg's center was measured. No significant change in blastoderm position due to centrifugation was noted.

In a further study, eggs (Hy-Line) were weighed, stored in fixtures for 5 days, spun for 30 minutes at 300 rpm (Beckman Allegra 6KR centrifuge) and then stored for a day prior to measuring the blastoderm position. An analysis of covariance was utilized that considered position as the dependent variable and centrifugation as fixed. As shown in Table 10 below, there were no significant differences in blastoderm position, and in fact the centrifuged eggs showed a blastoderm position slightly further from center.

TABLE 10

| Treatment | | Blastoderm position (mm) | Blastoderms too far off |
|---|---|---|---|
| Stored for 5 days, centrifuged, stored for a day. | Mean | 5.3005 | 2% |
| | SD | 3.0679 | |
| | n | 39 | |
| Not centrifuged | Mean | 5.1559 | 2% |
| | SD | 2.7494 | |
| | n | 48 | |

Turning.

The effect of turning the eggs during storage on blastoderm orientation toward the top center of the egg was evaluated. Eggs were placed in Hovabator turners at 60 F, 75% RH, for 6-7 days. The turners moved the eggs plus and minus 45 degrees from vertical and a complete cycle from 0 to +45 to 0 to −45 and back to zero took 4 hours. The no treatment eggs were stored in flats (cardboard) for comparison (to match the eggs in the turners). The results are shown in Table 11 below:

TABLE 11

| Treatment | | Blastoderm position (mm) | Blastoderms too far off |
|---|---|---|---|
| Turned | Mean | 3.6036 | 0% |
| | SD | 2.2245 | |
| | n | 46 | |
| BOVANS | | | |
| Not-Turned | Mean | 4.2386 | 0% |
| | SD | 2.4452 | |
| | n | 42 | |
| Turned | Mean | 5.5419 | 0% |
| | SD | 2.8708 | |
| | n | 60 | |
| HYLINE | | | |
| Not-Turned | Mean | 5.9126 | 0% |
| | SD | 2.6295 | |
| | n | 60 | |

Analysis of variance indicated that results between treatment groups were not significant for either Bovan or Hy-Line eggs, although the mean distance from the center was less for the turned eggs.

Spinning.

The effect of spinning the eggs during storage on blastoderm orientation toward the top center of the egg was evaluated. The eggs were stored in fixtures as described in Example 7 and were compared with eggs that were not spun but also stored in fixtures. For this trial, the eggs were stored for 5 days, spun for 30 minutes at 300 rpm, and then stored for a day prior to measuring blastoderm position. The spinning group had a slightly larger blastoderm position from center, although the percentage of blastoderms that were too far off center to be seen improved slightly. The results are in Table 12 below:

TABLE 12

| Treatment | | Blastoderm position (mm) | Blastoderms too far off |
|---|---|---|---|
| Spun | Mean | 5.7037 | 0% |
| | SD | 3.4034 | |
| | N | 43 | |
| BOVANS | | | |
| Not-Spun | Mean | 5.9170 | 0% |
| | SD | 3.4443 | |
| | N | 44 | |

Analysis of variance indicated that the results were not significantly different among treatment groups, although the mean distance from center was slightly less for the turned eggs.

Shaking.

Shaking the eggs during storage to orient the blastoderm toward the top dead center of the egg was investigated. The eggs were stored in fixtures as described in Example 6 and were compared with eggs that were not shaken but also stored in fixtures.

The diameter of the blastoderm was also measured while blastoderm position was measured for each of the different treatments described above. The results showed there was no change in blastoderm size with any of the treatments.

Although the foregoing invention has been described in some detail by way of illustration and example for purposes of clarity and understanding, it will be apparent that certain changes and modifications may be practiced within the scope of the appended claims and equivalents thereof.

That which is claimed is:

1. An avian egg processing method, comprising:
   orienting an avian egg containing a blastoderm in a predetermined position;
   introducing a small opening into a shell of the egg;
   introducing a small opening in an outer shell membrane of the egg under the small opening in the egg shell; and then
   extending a device through the small openings in the egg shell and the outer shell membrane so as to pierce an inner shell membrane with the device, wherein the inner shell membrane is essentially intact prior to inserting the device therethrough; and
   retracting the device from the egg.

2. The method of claim 1, wherein the device is a delivery device and the method further comprises the step, following said piercing step, of releasing a substance through the delivery device and depositing the substance into the egg.

3. The method of claim 2, wherein the device is a multiple injection delivery device.

4. The method of claim 2, wherein the substance to be deposited in the egg comprises a polypeptide.

5. The method of claim 4, wherein the polypeptide is selected from the group consisting of an antibody, hormone, growth factor, enzyme and cytokine.

6. The method of claim 2, wherein the substance to be to deposited in the egg comprises a nucleotide sequence.

7. The method of claim 6, wherein the nucleotide sequence is introduced into the blastoderm using a method selected from the group consisting of a viral vector, liposomes and electroporation.

8. The method of claim 6, wherein the nucleotide sequence encodes a polypeptide or an antisense nucleic acid.

9. The method of claim 2, wherein the substance to be deposited in the egg comprises an antibiotic.

10. The method of claim 2, wherein the substance to be deposited in the egg comprises a donor cell.

11. The method of claim 10, wherein the donor cell is an avian cell.

12. The method of claim 11, wherein the donor cell is selected from the group consisting of a chicken, turkey, duck, goose, quail, pheasant, parakeet, parrot, cockatoo, cockatiel, ostrich and emu cell.

13. The method of claim 11, wherein the donor cell is from a different avian species than the species of the blastoderm.

14. The method of claim 10, wherein the donor cell is a transgenic cell.

15. The method of claim 10, wherein the donor cell is selected from the group consisting of a blastodermal cell, stem cell, cultured stem cell, embryonic stem cell, primordial germ cell, embryonic germ cell, and any combination of the foregoing.

16. The method of claim 10, wherein the blastoderm is a chicken blastoderm and the donor cell is a chicken cell.

17. The method of claim 16, wherein the blastoderm and the donor cell are from different breeds or strains of chicken.

18. The method of claim 1, wherein the device is a sampling device and the method further comprises the step, following said piercing step, of removing a sample from the egg.

19. The method of claim 18, wherein the sample removed from the egg comprises subgerminal cavity fluid.

20. The method of claim 18, wherein the sample removed from the egg comprises blastodermal cells.

21. The method of claim 1, wherein the device is a detector device and the method further comprises the step, following said piercing step, of detecting with the detector device information from the interior of the egg.

22. The method of claim 21, wherein the detector device is an electrical sensor.

23. The method of claim 21, wherein the detector device is an optical sensor.

24. The method of claim 21, wherein the detector device is a chemical sensor.

25. The method of claim 21, wherein the detector device is a temperature sensor.

26. The method of claim 21, wherein the detector device is an acoustic sensor.

27. The method of claim 21, wherein the detector device is a pressure sensor.

28. The method of claim 1, wherein the device is extended through the small opening in the egg shell to a predetermined location.

29. The method of claim 1, wherein the device is extended through the small opening in the egg shell to a location in the blastoderm or in close proximity thereto.

30. The method of claim 29, wherein the device is extended through the small opening in the egg shell to a location selected from the group consisting of:
    (a) the subgerminal cavity,
    (b) between the area opaca and the vitelline membrane,
    (c) between the area pellucida and the vitelline membrane,
    (d) between the area opaca and the area pellucida,
    (e) in the area pellucida,
    (f) in the area opaca, and
    (g) any combination of (a) to (f) above.

31. The method of claim 1, further comprising the step of compromising the blastoderm.

32. The method of claim 1, wherein the egg is oriented in a generally horizontal position and the small opening in the egg shell is introduced into the upward facing side of the egg.

33. The method of claim 1, wherein the egg has been stored prior to treatment.

34. The method of claim 1, wherein the blastoderm is a stage XIII (Eyal-Giladi & Kochav) or earlier blastoderm.

35. The method of claim 34, wherein the blastoderm is a stage VIII to stage XIII (Eyal-Giladi & Kochav) blastoderm.

36. The method of claim 34, wherein the blastoderm is a stage X (Eyal-Giladi & Kochav) blastoderm.

37. The method of claim 1, wherein the egg is selected from the group consisting of a chicken, turkey, duck, goose, quail, pheasant, parakeet, parrot, cockatoo, cockatiel, ostrich and emu egg.

38. The method of claim 37, wherein the egg is a chicken egg.

39. The method of claim 37, wherein the egg is a turkey egg.

40. The method of claim 1, wherein the blastoderm comprises a heterologous nucleic acid.

41. The method of claim 1, further comprising the step of steering the blastoderm to a desired location.

42. The method of claim 41, wherein said steering step comprises a method selected from the group consisting of:
    (a) agitating the egg,
    (b) heating the egg,
    (c) holding the egg in a fixed position,
    (d) chemical treatment of the egg, and
    (e) any combination of (a) to (d) above.

43. The method of claim 1, further comprising the step of determining the location of the blastoderm or a compartment therein.

44. The method of claim 43 wherein said determining step comprises visualizing the blastoderm.

45. The method of claim 43, wherein said determining step comprises determining the location of the blastoderm or a compartment therein with a detector device.

46. The method of claim 1, further comprising the step of sealing the small opening in the egg shell.

47. The method of claim 1, further comprising the step of incubating the egg until hatch.

48. An avian egg processing method, comprising:
    orienting a blunt end of an avian egg in a predetermined position, the avian egg containing (i) a blastoderm and (ii) an air cell;
    introducing a small opening into a shell of the egg at the blunt end of the egg over the air cell;
    introducing a small opening in an outer shell membrane under the small opening in the egg shell; and then
    extending a delivery device through the small openings in the egg shell and the outer shell membrane so as to pierce an inner shell membrane with the delivery device, wherein the inner shell membrane is essentially intact prior to inserting the delivery device therethrough;
    releasing a substance through the delivery device and depositing the substance in a location in the blastoderm or in close proximity thereto; and
    retracting the delivery device from the egg.

49. The method of claim 48, wherein said orienting step comprises placing the blunt end of the egg in a generally upward position.

50. The method of claim 48, wherein the small opening in the egg shell at the blunt end of the egg is introduced in a predetermined location.

51. The method of claim 50, wherein the predetermined location is in substantially the center of the air cell.

52. The method of claim 48, wherein said steps of introducing a small opening in the egg shell and the outer shell membrane are carried out essentially concurrently.

53. The method of claim 48, further comprising the step of determining the location of the blastoderm prior to said releasing step.

54. The method of claim 48, wherein the delivery device is extended through the small opening in the egg shell to a location selected from the group consisting of:
(a) the subgerminal cavity,
(b) between the area opaca and the vitelline membrane,
(c) between the area pellucida and the vitelline membrane,
(d) between the area opaca and the area pellucida,
(e) in the area pellucida,
(f) in the area opaca, and
(g) any combination of (a) to (f) above.

55. An avian egg processing method, comprising:
orienting a plurality of avian eggs in a predetermined position, wherein each egg contains a blastoderm;
introducing a small opening into a shell of each egg;
introducing a small opening in an outer shell membrane of each egg under the small opening in the egg shell; and then
extending a delivery device through the openings in each egg shell and outer shell membrane so as to pierce an inner shell membrane of each egg with the delivery device, wherein the inner shell membrane is essentially intact prior to inserting the delivery device therethrough;
releasing a substance through the delivery device and depositing the substance in a location in the blastoderm or in close proximity thereto in each egg; and
retracting the delivery device from each egg.

56. The method of claim 55, further comprising the step of incubating the plurality of eggs to hatch.

57. The method of claim 56, wherein a resulting hatch rate is at least about 50%.

58. The method of claim 56, wherein a resulting hatch rate is at least about 65%.

59. An avian egg processing method, comprising:
orienting a blunt end of an avian egg in a predetermined position, the avian egg containing (i) a blastoderm and (ii) an air cell;
introducing a small opening into a shell of the egg at the blunt end of the egg over the air cell;
introducing a small opening in an outer shell membrane under the small opening in the egg shell; and then
extending a sampling device through the small openings in the egg shell and the outer shell membrane so as to pierce an inner shell membrane with the sampling device, wherein the inner shell membrane is essentially intact prior to inserting the sampling device therethrough;
removing a sample from the blastoderm with the sampling device; and
retracting the sampling device from the egg.

60. An avian egg processing method, comprising:
orienting a blunt end of an avian egg in a predetermined position, the avian egg containing (i) a blastoderm and (ii) an air cell;
introducing a small opening into a shell of the egg at the blunt end of the egg over the air cell;
introducing a small opening in an outer shell membrane under the small opening in the egg shell; and then
extending a detector device through the small openings in the egg shell and the outer shell membrane so as to pierce an inner shell membrane with the detector device, wherein the inner shell membrane is essentially intact prior to inserting the detector device therethrough;
detecting with the detector device information from the interior of the egg; and
retracting the detector device from the egg.

* * * * *